(12) United States Patent
Choi

(10) Patent No.: US 9,498,974 B2
(45) Date of Patent: Nov. 22, 2016

(54) DEVICE AND METHOD FOR PRODUCING A CUSTOMIZED COSMETIC COMPOSITION

(71) Applicant: Minkyung Grace Choi, Bayside, NY (US)

(72) Inventor: Minkyung Grace Choi, Bayside, NY (US)

(*) Notice: Subject to any disclaimer, the term of this patent is extended or adjusted under 35 U.S.C. 154(b) by 0 days.

(21) Appl. No.: 14/701,885

(22) Filed: May 1, 2015

(65) Prior Publication Data
US 2015/0314141 A1 Nov. 5, 2015

Related U.S. Application Data

(60) Provisional application No. 61/987,783, filed on May 2, 2014, provisional application No. 62/039,654, filed on Aug. 20, 2014, provisional application No. 62/086,425, filed on Dec. 2, 2014.

(51) Int. Cl.
| | | |
|---|---|---|
| *A61K 8/00* | (2006.01) |
| *B41J 3/407* | (2006.01) |
| *A45D 44/00* | (2006.01) |
| *A61Q 19/00* | (2006.01) |

(52) U.S. Cl.
CPC .............. *B41J 3/407* (2013.01); *A45D 44/00* (2013.01); *A61K 8/00* (2013.01); *A61K 2800/43* (2013.01); *A61K 2800/80* (2013.01); *A61K 2800/87* (2013.01); *A61K 2800/882* (2013.01); *A61Q 19/00* (2013.01)

(58) Field of Classification Search
CPC .... B41J 2/0057; B41J 3/4076; B41J 25/308; B41J 25/3088; B41J 29/393; B41J 3/407; A45D 44/00; A61K 2800/882; A61K 2800/87; A61K 2800/80; A61K 8/00; A61K 2800/43; A61Q 19/00
USPC ........................................................ 347/110
See application file for complete search history.

(56) References Cited

U.S. PATENT DOCUMENTS

| | | | |
|---|---|---|---|
| 5,641,809 A | 6/1997 | Hagen et al. | |
| 5,761,655 A * | 6/1998 | Hoffman | ............ G06F 17/3025 |
| 6,516,245 B1 * | 2/2003 | Dirksing | ............... A45D 40/00 |
| | | | 700/233 |

(Continued)

FOREIGN PATENT DOCUMENTS

| | | | |
|---|---|---|---|
| DE | 19707254 | 8/1998 | |
| FR | 2759941 A1 * | 8/1998 | ............. A45D 33/00 |

OTHER PUBLICATIONS

Instant Eyedropper Drops The Pain From Color Matching (online). Kidd, Jerry, Aug. 23, 2008 [retrieved Jul. 13, 2015 (Jul. 13, 2015)1. Retrieved from the Internet:<URL. http://www.makeuseof.com/tag/instant-eyedropper-drops-the-pain-from-color-matching/ p. 1, fourth paragraph; p. 2; second paragraph.

*Primary Examiner* — Manish S Shah
*Assistant Examiner* — Yaovi M Ameh
(74) *Attorney, Agent, or Firm* — Leason Ellis LLP

(57) ABSTRACT

A device for producing a cosmetic composition is in the form of a printer that is modified to receive and process cosmetic components. The device includes a printer housing that includes at least one print head and an opening for receiving a substrate and allow positioning of the substrate in relation to the at least one print head. At least one replaceable cartridge is provided and contains a cosmetic substance. The at least one replaceable cartridge is operatively coupled to the at least one print head such that the cosmetic substance can be applied to the substrate through the at least one print head. The resulting cosmetic composition is made of at least one cosmetic substance and the cosmetic composition is a transferable material that can be removed from the substrate and applied to a part of a human body.

26 Claims, 11 Drawing Sheets

(56) References Cited

U.S. PATENT DOCUMENTS

| | | | |
|---|---|---|---|
| 2007/0285467 A1* | 12/2007 | Tanaka | B41J 2/04528 347/60 |
| 2008/0080766 A1 | 4/2008 | Payonk et al. | |
| 2011/0151029 A1* | 6/2011 | Zheng | A61K 8/4906 424/725 |
| 2013/0302078 A1 | 11/2013 | Edgar | |
| 2013/0314471 A1* | 11/2013 | Brenner | B41J 2/16552 347/28 |

* cited by examiner

DEVICE AND METHOD FOR PRODUCING A CUSTOMIZED COSMETIC COMPOSITION

CROSS-REFERENCE TO RELATED APPLICATIONS

This application is based on and claims priority to U.S. provisional patent application Ser. No. 61/987,783, filed May 2, 2014, U.S. provisional patent application Ser. No. 62/039,654, filed Aug. 20, 2014, and U.S. provisional patent application Ser. No. 62/086,425, filed Dec. 2, 2014, the entire contents of all of which are incorporated by reference as if set forth herein in their respective entireties.

TECHNICAL FIELD

This invention relates to a device (printer) and method for producing a cosmetic composition in a customized manner at a low cost and further based, in one embodiment, on a pixel value (hexadecimal color code or based on other computer notation color codes). In addition, to the present invention relates to cosmetic products that can be formed using a variety of different pieces of equipment.

BACKGROUND

Today a wide range of cosmetic products are available in the consumer market. However, it is not easy to find a product that perfectly fits with one's taste and interest. First, the tone (e.g., color, lightness, etc.) and texture (e.g., dry, smooth, etc.) of each person's skin vary significantly. The appearance of skin also varies seasonally. Second, each individual has their own taste. Because makeup products, foundation or eye shadow for example, are applied directly to the human body, users, most of whom are women, tend to notice subtle differences in color and texture, which makes it hard to find a completely suitable color. Based on the foregoing, cosmetics come in a vast number of different colors and styles.

Further, even if one finds a perfect one, the price may be an issue. Unlike clothing on which you can try before purchase, you have to buy an entire unit to evaluate the matching of the makeup product, unless a small portion, or a sample, is available for free trial. However, cosmetic samples or free-application service over the counter are usually available only for expensive products that are sold in prestige outlets. As a result, it is not uncommon for users to throw away the cosmetic product after single use. In addition, inexpensive cosmetic products sold in mass outlets do not provide exclusive looks and/or provide a wide variety of colors. Additionally, after having discovered a desired cosmetic, having to travel to and from a store to purchase the item, then search for the item in store/online and proceed with the trial or returns process is cumbersome. Also, most stores carry a limited amount of colors/shades due to shelf space which increases increases the barriers to consumption and remote store locations, busy schedules and shipping times (for online orders) can increase the amount of time a consumer has to wait until they can consume the desired cosmetic product.

In order to meet various needs of makeup users, there exist some products and systems that provide custom color selection. For example, U.S. Pat. No. 7,121,429 issued to Bartholomew et al. discloses a cosmetic body powder selection system using a point of sale dispenser. Also known as "a makeup kiosk," this type of system allows a user to custom select color or dispense a color, effect or both, which is directly applied to the user. However, the system, which requires a bulky dispensing assembly unit (FIG. 3) and a viewing station (FIG. 1), is apparently for industrial use, not for personal use. An end user must travel to a sales site to purchase their service.

Similarly, U.S. Patent Publication No. 2011/0164263 published to Samain et al. discloses a method of automatically forming and applying a cosmetic deposit onto the skin or lips. The deposit has an optical characteristic, for example color or gloss, and it corresponds substantially to the measured optical characteristic of a body part (e.g., face). This system provides custom forming of cosmetic colors. However it also requires unique, sophisticated devices such as a custom-made printing apparatus called "handpiece." An end user must either own this apparatus, or travel to the site providing the application service. In either way, it does not appear to provide the makeup users with an economical solution.

On the other hand, U.S. Pat. No. 6,190,730 issued to Matsos et al. discloses a cost-effective cosmetic solution, namely, a disposable, single application package that is used as a cosmetic sampler. Although commercial entities such as cosmetic companies and beauty shops who handle a large volume of samplers may benefit from this technology, end users may not. Further, the product sample containing a make-up slurry is pre-selected before printing on a plastic film and there is no freedom for an end user to custom select the color.

Based on the foregoing, there is a need to provide a consumer with a convenient, easily customizable, low cost cosmetic product the color of which can be selected by the consumer, thus providing a truly customized, personalize product. It will be appreciated that the teachings described herein are not limited to a personal consumer setting but instead can be implemented in a commercial, retail, manufacturing, etc. setting.

SUMMARY

An object of the invention is to provide a device (printer) for producing a cosmetic composition in a customized manner at a low cost. Unlike some of the above examples, the printer of the present invention uses a consumer-type desktop printer, e.g., an ink jet printer, that has been modified in view of the object of the present application, to deposit cosmetic ingredients (substances) on a substrate, in response to the user selecting a final color of the resulting cosmetic composition. The printer can be a standalone device with its own computing system or a peripheral device to a computing device, such as a personal computer or mobile device and thus the entire system of the present invention allows a person to produce his or her own cosmetic product at home without purchasing any costly hardware. For example, a user can pick a color from an image (such as a photo) displayed on an Internet browser screen or a mobile device (e.g., smart phone or tablet), then produce a cosmetic product having the same color at home using the present equipment. In short, the present invention provides users with simple, inexpensive and convenient solutions to customizing and personalizing cosmetic products.

In accordance with one embodiment, a device for producing a cosmetic composition is in the form of a printer that is modified to receive and process cosmetic components. The device includes a printer housing that includes at least one print head and an opening for receiving a substrate (which may or may not have a cosmetic base material on it—base material may also be in cartridge form and may be sprayed before or at the same time as inks and glamourizing agents etc.) and allow positioning of the substrate in relation to the at least one print head. At least one replaceable cartridge is provided and contains a cosmetic substance. The at least one replaceable cartridge is operatively coupled to the at least one print head such that the cosmetic substance can be applied to the substrate through the at least one print head. The resulting cosmetic composition is made of at least one cosmetic substance and the cosmetic composition is a transferable material that can be removed from the substrate and applied to a part of a human body.

The present invention is thus directed, as discussed below, to a method for producing a custom cosmetic product comprising the step of:

determining a first value representative of a color in accordance with a selection of one or more pixels on a display;

converting the first value to a second value that can be processed by a device that is configured to produce the cosmetic composition, wherein the device comprises a printer that is configured to receive a cosmetic component that includes a base material (either in a substrate platen area or cartridge area); and producing the cosmetic composition by applying one or more coloring agents in accordance with the second value onto the base material to form the selected color, the one or more cosmetic substances including at least one coloring agent, wherein the cosmetic substances are contained in individual cartridges that are in fluid communication with a respective print head and as discharged through the print head onto a surface of the base material (or if the base material is in a cartridge can also mix in with the base material at the same time if the base material is not previously dispensed (sprayed) before).

In one embodiment, the first value comprises an RGB value; the second value comprises a CMYK value

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF CERTAIN EMBODIMENTS

Figure 1:
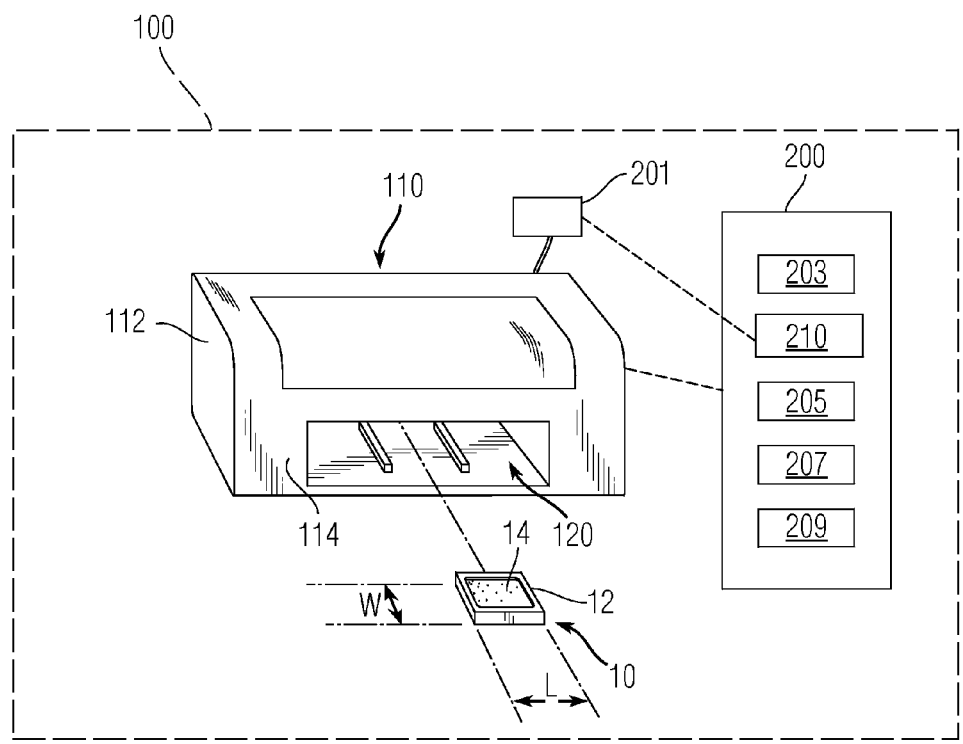
FIG. 1 is a top and side perspective view of a device (applicator) in accordance with one embodiment of the present invention showing a cosmetic component (substrate) exploded therefrom.
Figure 2:
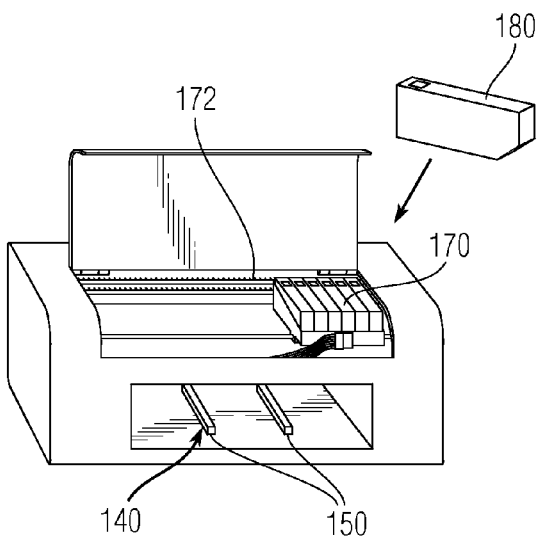
FIG. 2 is a top and side perspective view of the device with a top door open to show a print head assembly that includes a series of cartridges that dispense materials, such as liquid inks.

With reference to the drawings, FIGS. 1 and 2 show an embodiment of a system 100 for producing a customizable cosmetic product. As described herein and unlike a number of complex conventional cosmetic production systems, the system 100 is configured to be used by the end user (consumer). Not only does the system 100 allow the consumer to select and personalize the color of the cosmetic product but also achieves this result at lower cost compared to equivalent cosmetic products available at retail stores. It also provides more convenience than retail stores because the present system is in individual homes and people do not have to travel to stores to make their cosmetic purchases. Additionally, the system can be mobile and thus can be easily transported. The present system also provides more color selection/choices as well as design options because there is leverage between technology and the internet which provides nearly unlimited options. The system 100 is also configured to produce different types of cosmetic products using the same basic equipment.

The system 100 includes a device 110 for producing the customizable cosmetic product. In the illustrated embodiment, the device 110 is configured to apply one or more cosmetic ingredients or substances to a specific target location as part of the process for producing the end cosmetic product (cosmetic composition). In one exemplary embodiment, the device 110 is in the form of a printer or the like. As is known, a printer is typically understood to be a peripheral device which forms an image/representation on physical media, such as paper or other physical material. Individual printers are designed to support local and network users in that a series of printers can be part of a network. There are many types of printers commercially available and typically, printers are classified by the printer technology that they employ, such as toner-based printers, liquid inkjet printers, solid ink printers, etc. In accordance with the present invention, the device 110 can be thought of as a printer in the sense that the device 110 deposits one or more substances (dyes, pigments, etc.) at a very specific location of an underlying substrate to create the chosen desired color that is formed on the substrate and provide other effects.

As discussed herein, the device 110 can be a standalone unit having an integral computing device and/or user interface that allows the user to enter the color code information as by entering the data via an input device and/or making a selection by means of a screen that is an integral part of the device 110.

In accordance with the present invention, any suitable printer 110 can be used so long as the printer 110 deposits coloring agents and other materials that are suitable for use in cosmetic products. In one embodiment, the printer 110 is an inkjet printer which functions as a conventional inkjet printer in that it operates by propelling variably sized droplets of liquid ink/pigment (coloring agent). Ink jet printing, which includes so-called "continuous ink jet" and "drop on demand" technologies, can be used.

While the printer 110 has many attributes of a consumer printer for use in the workplace, the printer 110 is modified (customized) in view of the intended application and more specifically, in view of the objective of producing cosmetic products. For example, the printer 110 has a housing 112 that contains the working components of the device 110 and is configured to have an opening 120 for receiving a cosmetic component 10 (a substrate) that is used to produce the final resulting cosmetic product. Unlike conventional paper printers, the device 110 does not advance paper and therefore, does not require a paper feeder mechanism. Instead, as described herein, the opening 120 receives the cosmetic component 10 and allows the cosmetic component 10 to be positioned in a target location/position. The cosmetic component 10 contains a cosmetic substance. As shown, the opening 120 can be in the form of an opening that is formed along a front 114 of the housing 112. The opening 120 is preferably not only sized to receive the cosmetic component 10 but also receive a hand of a user to allow the insertion and positioning of the cosmetic component 10 within the hollow interior space of the housing 112.

Figure 4:
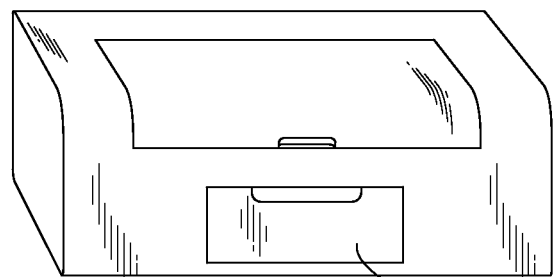
FIG. 4 is a top and side perspective view of a device (applicator) in accordance with another embodiment of the present invention.
Figure 5:
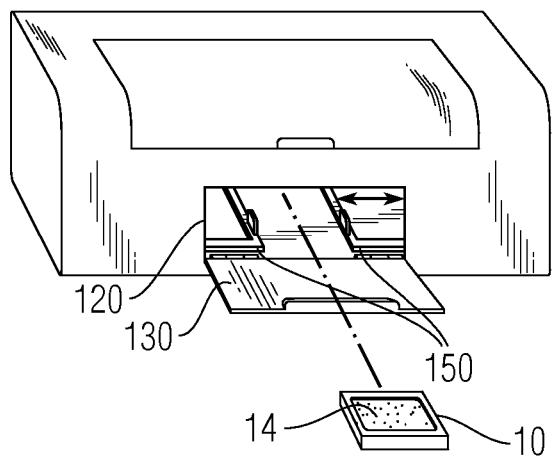
FIG. 5 is a top and side perspective view of the device of FIG. 4 with a front door open and a cosmetic component being exploded therefrom.

The opening 120 can be optionally covered with a door 130 (See FIGS. 4 and 5). The door 130 is movable between an open position and a closed position. The door 130 can open about an axis (pivot) and in the open position, the door 130 can lie generally flush with the surface on which the printer 110 rests.

Alternatively, the door 130 can be eliminated and the opening 120 is permanently open and accessible as in FIG. 1.

Unlike traditional printers, the cosmetic component 10, which represents a substrate (which can include a base material) on which other cosmetic ingredients are applied, as discussed herein, is both inserted and withdrawn from the device 110 through the same opening 120. In conventional printers, paper is inserted into the printer at a first feeder location and is withdrawn from the printer at a second feeder location. As discussed herein, one of the many differences between the device 110 and a traditional printer is that in at least a number of embodiments, the cosmetic component 10 remains stationary (or at least substantially stationary) during the application of the coloring agents and other materials onto the material of the cosmetic component 10. The substrate 10 is only removed after the application process is completed.

The device 110 can further include one or more guides 140 to assist the user in inserting the cosmetic component 10 within the interior of the device such that it assumes the target location/position. For example, as shown in FIG. 2, the guides 140 can be in the form of rails 150 spaced apart from one another. The rails 150 protrude from a floor of the device 110 and serve to ensure proper positioning of the cosmetic component 10 (substrate) as by the user placing the cosmetic component 10 between the rails 150 and sliding the cosmetic component 10 along the floor until the cosmetic component 10 contacts a stop (not shown). Once the cosmetic component 10 contacts the stop, the cosmetic component 10 is in the target location which ensures proper application of the coloring agents and other materials onto the material of the cosmetic component 10.

FIG. 5 shows an embodiment in which the guides 140 are adjustable to accommodate different sized cosmetic components 10. Any number of mechanisms can be used to lock the guides 140 in a set location. For example, the rails 150 can include depressable tabs that allow movement of the rails 150 in certain directions, such as side-to-side (lateral) (Y axis), thereby accommodating different sizes of cosmetic components 10. The rails 150 can also be configured to move in a forward-to-rear direction (X axis).

Figure 3:
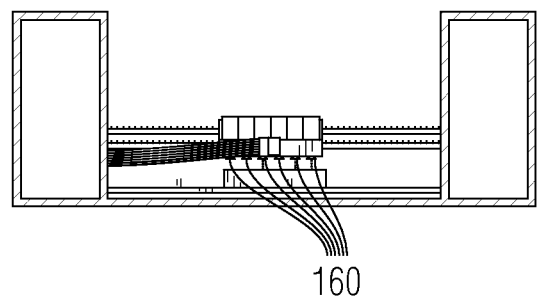
FIG. 3 is a cross-sectional view of the printer in which the substrate is placed in relation to the individual cartridges.

The device 110 also has a mechanism (means) for delivering the one or more coloring agents and/or additional material to the base material of the cosmetic component 10 or alternatively, as described herein, the base material can likewise be delivered to the mechanism. For example, when the device 110 is in the form of a printer, a print head 160 (FIG. 3) is provided and is configured to dispense (discharge) a material, such as a coloring agent or other cosmetic ingredient, or even the base material, etc., onto the surface of the material of the cosmetic component 10 or onto an empty compartment of the substrate. Depending upon the print technology employed, the print head 160 can be a fixed print head or a disposable print head. Fixed print heads are designed to last for the life of the printer and includes one or more fine nozzles through which the ink (or other material) is discharged. Disposable print heads are designed as part of the replaceable ink cartridge as described herein and thus, are disposed within the cartridge when the ink is entirely consumed or the cartridge is otherwise inoperable. Alternatively, the cartridge can be of a refillable type and removable.

FIG. 2 shows a disposable (refillable) print head design in that the print mechanism includes a movable carriage 170 that interlockingly receives and holds one or more cartridges 180. The carriage 170 is operatively connected to a drive, such as a stepper motor, that causes controlled movement of the carriage 170 along a rail 172. The rail 172 extends across the device 110 within the hollow interior above the floor. The rail 172 is thus a linear rail. The carriage 170 is open along its top to allow for easy insertion and removal of the cartridges 180 into specific set locations. For example, the carriage 170 typically includes a set of slots that are identified for receiving specific cartridges 180 (i.e., cartridges that contain specific colors as discussed below). Typically, the cartridges 180 are snap-fit within the carriage 170. The placement of the cartridges 180 within the carriage 170 thus positions the individual cartridges 180 at specific, set locations that are known by the printer software executed by the device 110.

In one embodiment, a number of the cartridges 180 contain inks that are suitable for cosmetic applications. For example, the cartridges 180 can contain the following inks: cyan (C), black (K), magenta (M), and yellow (Y). Each cartridge 180 holds only one color or alternatively, one cartridge can contain more than one color with each separated from the other. It will be appreciated that some print technology uses more than four cartridges 180 and can include other color cartridges such as, light magenta and light cyan. The carriage 170 thus can contain more than four slots to receive additional cartridges including a cartridge containing the base material as described herein. Further, as discussed herein, the carriage 170 can receive not only ink cartridges for applying black and/or colored ink onto the material of the cosmetic component 10 but can also receive non-ink cartridges. For example, a scent containing cartridge that contains a perfume or a cartridge that provides other effects. Additionally, bulking material or other additives can be supplied from a cartridge (e.g., a wax containing cartridge or an oil containing cartridge). As mentioned herein, depending on whether the printer is of a fixed or disposable head design, the cartridge 180 may contain the print head and nozzle(s) for discharging the ink or there may be a fixed print head in close proximity to the cartridge for receiving and discharging the contents (ink) of the cartridge.

In any event, the print head contains a series of nozzles that are to spray very fine drops of ink or other material onto the substrate. Inkjet printing involves a print mechanism that is of a non-impact printing type in that the printer does not touch the substrate (here the cosmetic component 10) when discharging the ink. Different types of inkjet printers form their droplets in different ways and more specifically, there are two main inkjet technologies, namely: thermal bubble and piezoelectric technology. Either technology can be used in accordance with the present invention.

In accordance with one embodiment, the print head 160 is configured to spray each substance contained in one cartridge 180 across at least one dimension of the substrate (material of the cosmetic component 10). For example, the cosmetic component 10 can be thought to have a length (L) and a width (W) as identified in FIG. 1. The length (L) can be equal to, less than or greater than the width (W). The carriage 170 and cartridges 180 thus travel along the rail 172 which extends the length (L) of the cosmetic component 10. In other words, an axis extending the length (L) of the cosmetic component 10 is parallel to the axis of the rail 172. The print head 160 preferably has a spray coverage that is at least equal to the width (W) of the cosmetic component 10 so as to allow application (spraying) of the cosmetic ingredients contained within the cartridges 180 across the entire width or at least across substantially the entire width of the cosmetic component 10. As mentioned herein, the carriage 170 and the cartridges 180 are driven along the rail 172 so as to permit the entire length of the cosmetic component 10 to be sprayed with ink and this in combination with the ability of the print head 160 to spray the ink across the entire width (or at least substantially the entire width), allows the entire surface of the material of the cosmetic component 10. This allows saturation of the surface and allows proper colorization of the material that forms the cosmetic component 10. As described herein, the software that controls the print operation can allow input of identification information concerning the cosmetic component 10 and based on such inputted information, the print head 160 is driven across the footprint of the cosmetic component 10 and the discharged material (e.g., liquid ink/dye) is only deposited across the footprint of the cosmetic component 10. Preferably, the material (ink, etc.) is applied from the print head(s) 160 in such a manner that a borderless dyed surface is formed as part of the cosmetic component 10 (in other words, it is preferred that the entire surface of the material 14 (cosmetic substance) is coated with applied inks or other applied materials from the print heads 160. Such identification information can be contained within a database stored in memory. This eliminates or reduces waste of the applied material and also ensures that a clean cosmetic product is formed. Alternatively, a non-color diluting base material (e.g., calcium carbonate, mica) can be used instead to still have an end product with uniform color; however, additional mixing will be necessary after printing. The use of calcium carbonate has an advantage in that it does not dilute the colors that are applied to the base material.

Traditional sensors (microchips) and the like can be part of the cartridges 180 to sense and indicate when the ink in the reservoir falls below a certain level. A display (LCD) can display such information to the user. In one preferred embodiment, the cartridge 180 is a reusable, refillable plastic reservoir tray for ink which the consumer refills with ink as necessary. A refillable cartridge is preferred in this environment given the amount of ink (or other material) that is needed to form the cosmetic composition from the base material. In contrast to traditional paper printing in which a relatively small amount of ink is used, the ink consumption in the present invention is much greater. For example, using a modern compact inkjet printer (e.g., a Canon ip110), it takes approximately 9 inches of continuous printing to saturate approximately 1 mm depth of calcium carbonate and approximately 0.05 of mica.

In addition, the print head should also be easily removable so that nozzles can be easily flushed and cleared in the event of a clog.

As in traditional inkjet printers, the carriage 170 is controllably driven back and forth along the rail 172 and ink is emitted from nozzles while they pass over the substrate (e.g., the stationary cosmetic component 10). The operation of device 110 is easy to visualize: liquid ink in various colors is squirted onto the surface of the material of the cosmetic component 10 to build a predetermined color selected by the user. Using the printer's motor assembly to move it from left to right and back again, the print head 160 is driven. There are several types of inkjet printing. The most common is "drop on demand" (DOD), which means squirting small droplets of ink onto the substrate through tiny nozzles. The amount of ink propelled onto the page is determined by the print driver software that dictates which nozzles shoot droplets, and when.

Additional details concerning exemplary print driver software and other software are described below.

As shown in FIG. 1 and other figures, the cosmetic component 10 includes a carrier 12 that holds a cosmetic material 14. The cosmetic material 14 can be any number of different types of cosmetic materials so long as they are suitable for application to human skin, etc. The cosmetic material 10 can take any number of different forms including solids (e.g., a solid base material, packed powder, loose powder, etc.); liquids; gels; emulsions; creams; etc., and can have any properties such as a fragrance, pearlescent, shimmer, sparkle, etc.

The material 14 can represent a dyeable base material that can be selected from the group consisting of: a powder (mica, titanium dioxide, calcium carbonate, talc, etc.), oil, wax, ester, water, cream, lotion, emulsion, a solid, and mixtures thereof. In one embodiment, the ester is selected from the group consisting of: isopropyl lanolate, myristyl lactate and octyl hydroxystearate. In any event, the material 14 can be broadly thought of as a cosmetic base or foundation that is suitable for application to the human body for a cosmetic purpose. It will therefore be appreciated that the device 110 is configured to allow the material 14 to be colored according to a color selected by the user and/or be otherwise customized by the user (e.g., application of scent, etc.). The device 110 thus serves to dye or otherwise apply a preselected color to the surface of the material 14 and since the material 14 is dyeable or otherwise can assume the color of the applied dye (pigments, inks, etc.), the device 110 causes the cosmetic material 14 to change color from the base color (white, light brown, cream, etc.) to the color selected by the user. As described below, the print driver software allows the user to select from a vast number of different colors and thus, the user can create a cosmetic product that has the precise color of their choice.

It will be appreciated that the material (base material) 14 has a thickness and there is a relationship between the thickness of the material 14 and the amount of ink (dye) or other material that is deposited onto the material 14 in order to ensure that the material is dyed and it assumes the color selected by the user. In other words, the cosmetic substances (in this case inks) are applied to the material 14 at an amount that allows for the cosmetic substances (inks) to be uniformly dispersed throughout the material 14. Thus, the total amount of ink deposited from all of the cartridges 180 is preferably sufficient to dye all of the material 14. The exact dying process and mechanism will vary depending upon the type of material 14 that is being used. For example, when the material 14 is a pressed powder (or semi-solid), the liquid inks will flow and disperse throughout the material 14. When the material 14 is a gel or cream, dyes (inks) will also disperse through the material 14; however, to ensure optimal uniformity, the user may need to mix the material 14 after application of the dyes (inks). Alternatively and optionally, the system 100 can have an automated mixing mechanism, such as being incorporated in the device 110, for mixing the contents in the substrate 10 without requiring manual mixing by the user.

The thickness of the material 14 can also vary depending upon the cosmetic product being formed and more particularly, whether the final cosmetic product is a powder type makeup (e.g., eye shadow, blush, finishing powder, etc.) or a cream/fat/lotion/oil/wax/varnish based makeup (e.g., lipstick, foundation, lip gloss, cream eye shadow, nail polish, etc.).

In any event and according to one embodiment, the print drive software and other software associated with the computing device calculates the proper amount of ink to be applied given certain parameters, such as the type of material 14 being used, the total amount of the material 14 present, the surface area of the material 14 and other spatial parameters of the material 14. The proper amount of ink is thus the amount of ink that causes the material 14 to assume the color selected by the user.

In accordance with at least one embodiment of the present invention, the device 110 thus dyes the material 14 to create the final cosmetic composition. In another embodiment, described herein, the dyes and the base material and any other materials are dispensed onto an empty holder (substrate) to form the cosmetic composition.

Figure 9:
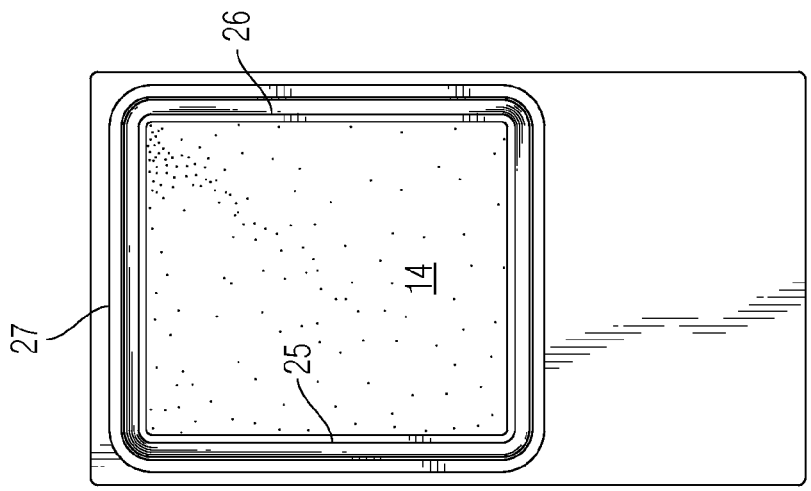
FIG. 9 is top perspective view of one exemplary substrate including a runoff trench.
Figure 9:
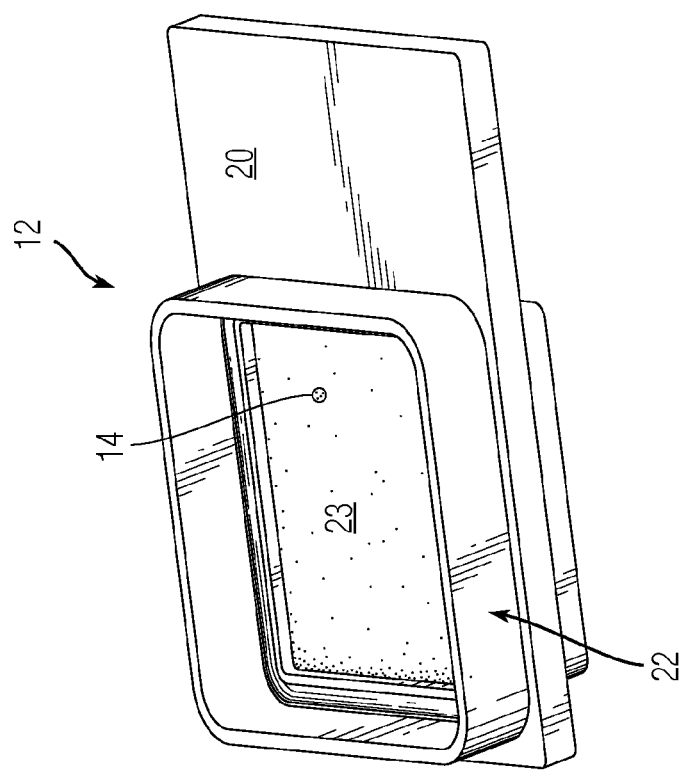

FIG. 9 shows one carrier 12 in the form of a plastic holder that has a first planar portion 20 which can be grasped by the user to hold and transport the carrier 12 and a second portion 22 which includes a well 23 that contains the material 14. The well is defined by a raised peripheral wall 25 that extends around the well and external to the wall 25, there is a runoff perimeter trench 26 that represents a recessed channel or space between wall 25 and an outer wall 27. The runoff perimeter trench 26 collects any sprayed ink that runs off of the material 14 or is otherwise sprayed onto the wall 25 outside of the material 14, etc.

As used herein, the term "printing" means delivering one or more cosmetic substances (such as inks, dyes, etc.) onto the surface of the substrate (e.g., material 14 of the cosmetic component 10 or onto an empty tray). After the cosmetic substance(s) is applied to the substrate through the print head(s), a cosmetic composition is formed by the dying/mixing of the one or more cosmetic substances with the material of the substrate. The formed cosmetic composition is a transferable material that can be removed from the substrate and applied to a part of a human body. Conventional makeup tools, such as a brush, puff or sponge can be used to remove the cosmetic composition off the substrate (carrier).

As mentioned herein, the cosmetic substances applied by the print head to the substrate are all safe and suitable for use as cosmetic products to be applied to the human body. In order to change the color of the base material 14 of the substrate (cosmetic component 10) at least one cosmetic substance comprises a coloring agent (which can be thought of as the ink of the inkjet printing process). The coloring agent is a material selected from the group consisting of: a natural dye, synthetic colorant, coal tar, chromium oxide, aluminum powder, manganese, iron oxide, mica flakes and FDA-approved cosmetic color additives listed in 21 C.F.R. Part 73, Subpart C such as caramel or β-carotene; or any other substances that can cause a change in the color of the base material 14.

In the case of using the device 110 as a traditional inkjet printer, the cartridges 180 can include: a cyan colored dye (C), a black dye (K), a magenta colored dye (M), and a yellow colored dye (Y). In the same way that an inkjet printer forms a colored image on a piece of paper, the device 110 forms a specifically colored substrate material (base material) by mixing the proper amounts of the various dyes to achieve this color.

The cosmetic substance applied via the device 110 can further comprise at least one bulking agent and at least one additive. The additive is a material that adds additional values to the cosmetic composition and is selected from the group consisting of; fragrance, preservative, pearlescent, sparkle, and shimmer. The bulking agent is used to provide even coverage on the human body part and usually has a smooth, slippery texture that makes the cosmetic composition easier to apply. The bulking agent can be a material selected from the group consisting of; talc, silk powder, silk fiber, nylon, wax, cream, ester and oil and mixtures thereof.

The device 110 can further include one or more sensors that sense the position of the substrate 10 and confirm that the substrate 10 is in the proper position below the print head 160. Such sensor can be an optical sensor or any other type of sensor.

The system 100 is a computer implemented system. As shown in FIG. 1, the system 100 includes one or more computing devices 200. The computing device 200 can be in the form of a personal computer, a mobile device, a tablet, a work pad, etc. The computing device 200 includes one or more processors used to execute software code in order to control the operation of data processing apparatus, read only memory (ROM), random access memory (RAM) or any other suitable volatile or non-volatile computer readable storage medium, which can be fixed or removable. The system 200 also includes one or more network interfaces 203 to transmit and receive data to and from other computing devices across a communication network. The network interface 203 can be any interface that enables communication between the any of the devices (e.g., 110) shown in FIG. 1 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting the devices and/or communication networks, such as private networks and the Internet. Such connections can include a wired connection or a wireless connection (e.g., using the IEEE 802.11 standard known in the relevant art) though it should be understood that network interface 203 can be practically any interface that enables communication to/from the processor.

We also be appreciated that the device 110 can include the computing device 200 in that the device (printer) 110 can be a standalone device that includes a user interface or the like that allows the user to directly enter color code information and other information, such as identification information relating to the substrate. In this embodiment, the device 110 can include means for communication with a network, such as the web, and preferably includes a display screen. The display screen can be used to select the target color and/or display the selected target color for confirmation by the user. Other features of the computing device 200 described below can be equally present in this configuration when the computing device 200 is an integral part of the device 110.

The computing device 200 includes memory 207.

Storage device(s) 205 can be included such as a hard disk drive, floppy disk drive, tape drive, CD-ROM or DVD drive, flash memory, rewritable optical disk, rewritable magnetic tape, cloud storage, or some combination of the above for storing program code, databases and application code. In certain implementations, memory 207 and/or storage device(s) are accessible by the processor, thereby enabling the processor to receive and execute instructions stored on the memory 207 and/or on the storage 205. Further, elements include one or more input devices such as a keyboard, mouse, track ball and the like, and a display 209. The display 209 can include a screen or any other such presentation device that enables the system to instruct or otherwise provide feedback to the user regarding the operation of the system (100). By way of example, display 209 can be a digital display such as an LCD display, a CRT, an LED display, or other such 2-dimensional display as would be understood by those skilled in the art. By way of further example, a user interface and the display 209 can be integrated into a touch screen display. Accordingly, the display is also used to show a graphical user interface, which can display various data and provide "forms" that include fields that allow for the entry of information by the user. Touching the touch screen at locations corresponding to the display of a graphical user interface allows the user to interact with the device to enter data, control functions, etc. So when the touch screen is touched, interface communicates this change to processor, and settings can be changed or user entered information can be captured and stored in the memory.

One or more software modules can be encoded in the storage device(s) 205 and/or in the memory 207. The software modules can comprise one or more software programs or applications having computer program code or a set of instructions executed in the processor. Such computer program code or instructions for carrying out operations or aspects of the systems and methods disclosed herein can be written in any combination of one or more programming languages, as would be understood by those skilled in the art. The program code can execute entirely on one computing device (e.g., data processing apparatus) as a stand-alone software package, partly on one device and partly on one or more remote computing devices, such as, a user computing device, or entirely on such remote computing devices. In the latter scenario, the various computing devices can be connected to the media server data processing apparatus through any type of wired or wireless network, including a local area network (LAN) or a wide area network (WAN), or the connection can be made to an external computer (for example, through the Internet using an Internet Service Provider). It should be understood that in some illustrative embodiments, one or more of the software modules can be downloaded over a network from another device or system via the network interface 203. For instance, program code stored in a computer readable storage device in a server can be downloaded over a network from the server to the storage 205.

The system 100 thus includes software that allows the device 110 to operate and permits the user to select the color that is to be applied to the substrate. Since the device 110 is merely a piece of hardware that receives and executes "printing related" commands, the device 110 works with software and drivers to process and carry out the print commands of the user. In particular, the computing device 200 can include a printer driver(s) 210 that communicates with printer firmware 201 associated with the device (printer) 110.

The print driver 210 works with a translator or the like to translate user commands into a language that the printer understands, directs the printer what to do with the command, manages other tasks that the printer might be doing, and instructs the printer to carry out the commands of the user.

As mentioned herein, the system 100 is configured to allow a user to produce a personalized cosmetic product that has a color that is specifically chosen by the user. The user interface, includes the one or more input devices and/or the display 209, and allows the user to select the color for the cosmetic product and also to preferably enter other relevant information, such as the type of cosmetic material that is being colored (dyed) and also other physical characteristics, such as the size of the cosmetic component 10, etc.

In contrast to other systems, the present system, according to one embodiment, is configured such that a pixel value of one or more pixels is used to produce the final cosmetic product (component 10). Each of the pixels that represents an image stored inside a computer has a pixel value which describes how bright that pixel is, and/or what color it should be. In the simplest case of binary images, the pixel value is a 1-bit number indicating either foreground or background. For grayscale images, the pixel value is a single number that represents the brightness of the pixel. The most common pixel format is the byte image, where this number is stored as an 8-bit integer giving a range of possible values from 0 to 255. Typically zero is taken to be black, and 255 is taken to be white. Values in between make up the different shades of gray. To represent color images, separate red, green and blue components must be specified for each pixel, and so the pixel 'value' is actually a vector of three numbers. Often the three different components are stored as three separate 'grayscale' images known as color planes (one for each of red, green and blue), which have to be recombined when displaying or processing. Multi-spectral images can contain even more than three components for each pixel, and by extension these are stored in the same kind of way, as a vector pixel value, or as separate color planes.

The actual grayscale or color component intensities for each pixel may not actually be stored explicitly. Often, all that is stored for each pixel is an index into a colormap in which the actual intensity or colors can be looked up.

Although simple 8-bit integers or vectors of 8-bit integers are the most common sorts of pixel values used, some image formats support different types of value, for instance 32-bit signed integers or floating point values. Such values are extremely useful in image processing as they allow processing to be carried out on the image where the resulting pixel values are not necessarily 8-bit integers. If this approach is used then it is usually necessary to set up a colormap which relates particular ranges of pixel.

The present invention is thus directed, as discussed below, to a method for producing a custom cosmetic product comprising the step of:

determining a first value representative of a color in accordance with a selection of one or more pixels on a display;

converting the first value to a second value that can be processed by a device that is configured to produce the cosmetic composition, wherein the device comprises a printer that is configured to receive a cosmetic component that includes a base material; and producing the cosmetic composition by applying one or more coloring agents in accordance with the second value onto the base material to form the selected color, the one or more cosmetic substances including at least one coloring agent, wherein the cosmetic substances are contained in individual cartridges that are in fluid communication with a respective print head and as discharged through the print head onto a surface of the base material.

In one embodiment, the first value comprises an RGB value; the second value comprises a CMYK value; the first value includes a brightness component and a color component; the cosmetic composition has a color represented by the second value; and the step of determining a first value comprises using a computing device to select the one or more pixels.

Thus, the present invention involves processing user selected digital color code information to form the color of the final cosmetic composition. Any number of different digital color code protocols can be used so long as the color code information reflects the pixel value of one or more pixels selected (highlighted) by the user.

Figure 10:
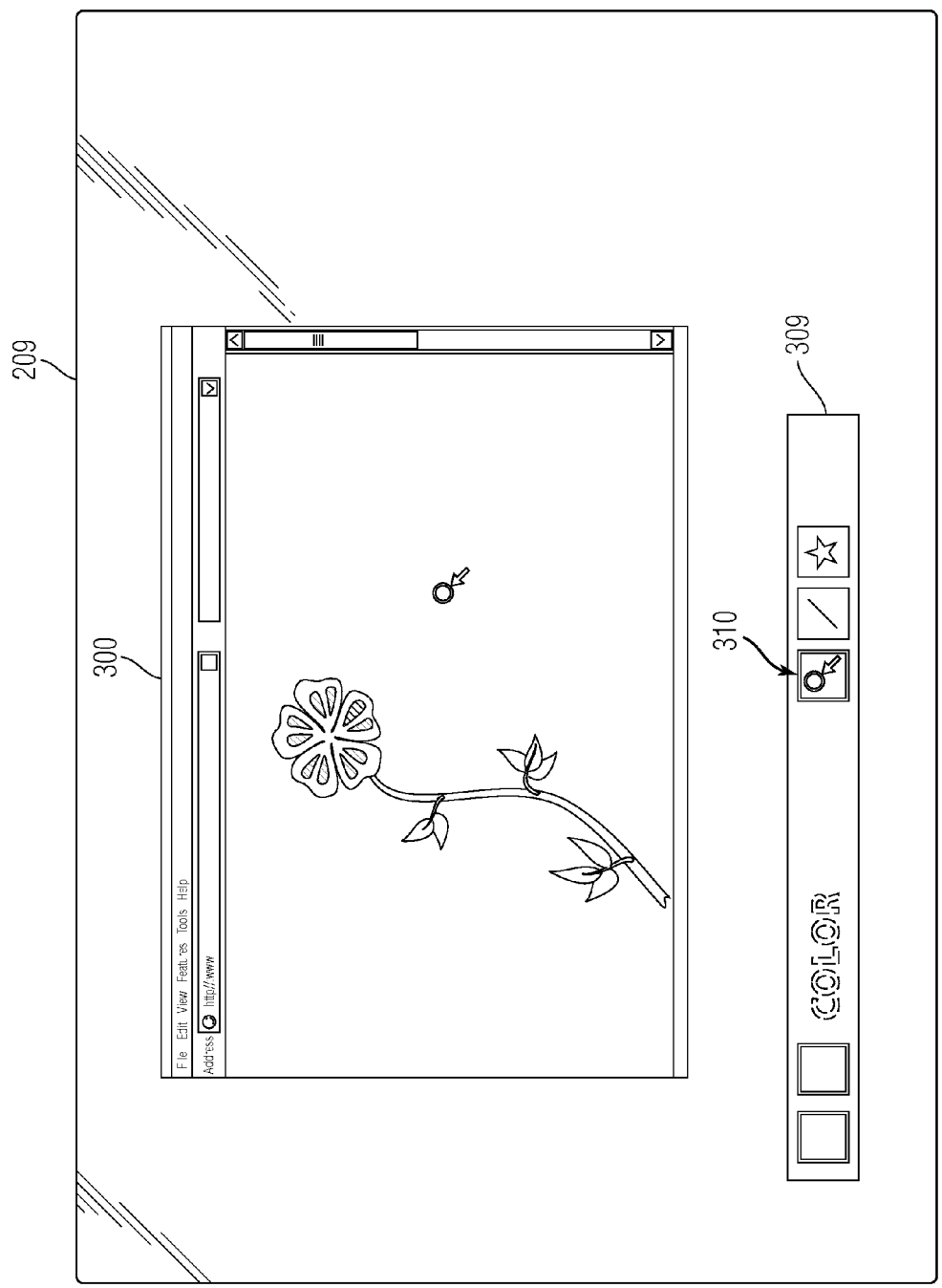
FIG. 10 is one exemplary screen shot showing a color selector tool (e.g., an eyedropper—hexadecimal color code identifier or other computer notation color code identifier)
Figure 11:
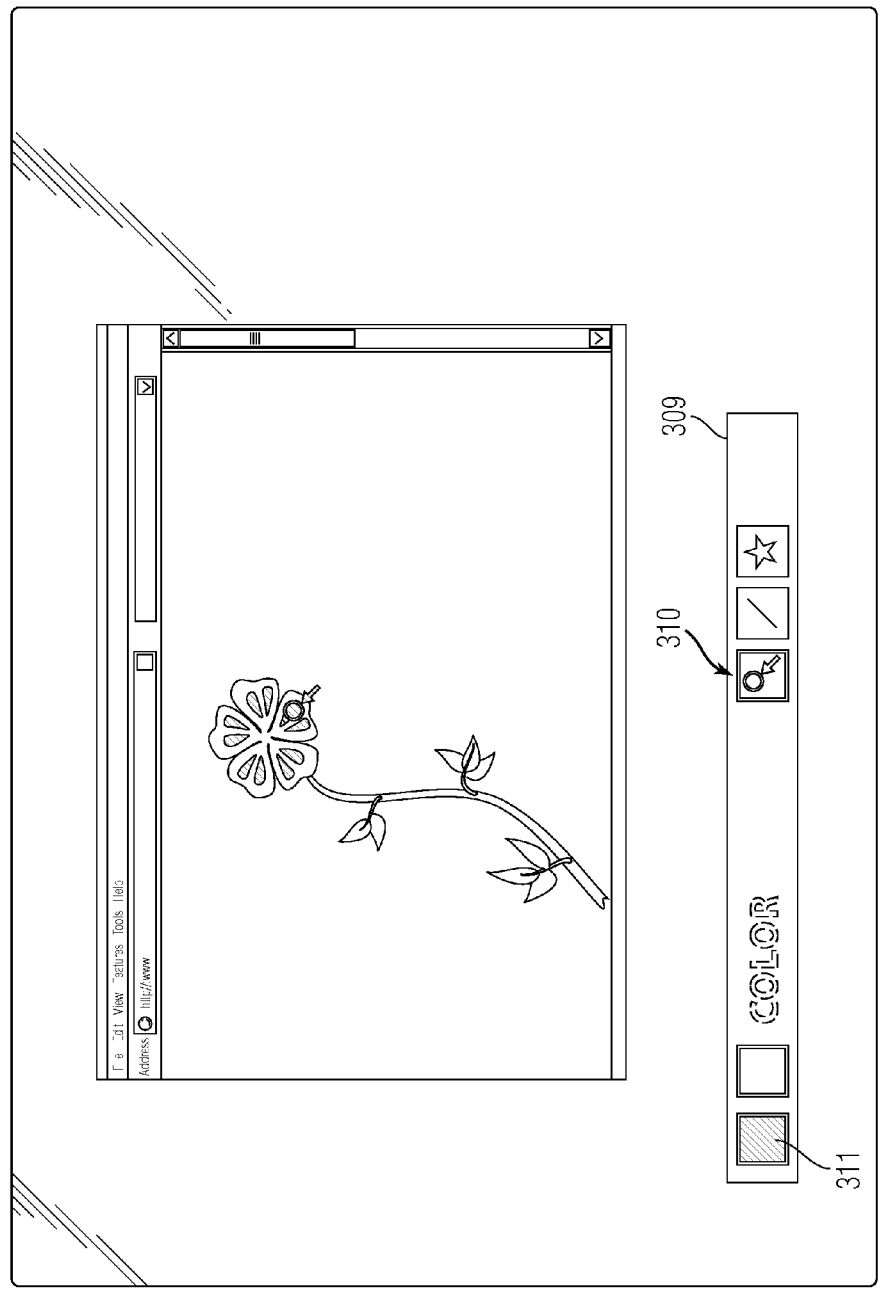
FIG. 11 is a screen shot showing a pointer positioned over a selected portion of an image that has the color of interest (as shown, the pointer is selecting a particular pixel or point (which is the smallest element on a display) to identify that pixel's hexadecimal (or other) color code identifier.

Referring to FIGS. 10 and 11, a web browser software application 300 is executed and displayed on the display screen 209. It will be understood that the web browser software application 300 can be configured as a mobile app (see below) or other suitable software. The web browser software application 300 includes one or more tools 310 for selecting the final color of the cosmetic product being produced (fabricated) by the user. The tools 310 can be accessed via a browser tool bar 309, a pull down menu, etc. For example, one tool 310 can be an eyedropper software tool that identifies and automatically pastes to the clipboard the HTML color code of any pixel on the screen with just a single mouse click. The tool 310 can be accessed along the tool bar 309 and in particular, the tool bar 309 can include an icon or pull down menu in which the tool 310 is accessed.

First, the user finds a color that is of interest and is represented as part of one or more colors. The color can be part of an image, such as a photograph, or image that is available on the web (e.g., displayed as part of a web page). In the case of a personal photograph, the user can upload the photo to the computer such that the photo is digitized and represented in digital form on the screen 209. The photo can be saved in the memory. The image (photo, etc.) can also be stored on a storage device. Once the image is displayed on screen 209, the user can use tool 310 to gather the color code information of a selected color.

It will also be appreciated that the user can enter the color code information without the use of tool 310 (eyedropper) and instead use one or more of the input devices, such as a keyboard, etc. For example, if the user knows the color code information, the user can input such information into a software program that then executes print commands to cause dispensing on the inks/dyes, etc. The color code information can thus be stored in memory in a database and can be accessed by the user.

Once the tool 310 is launched, the tool works by moving the mouse pointer 211 to a pixel (the smallest component of the display screen) whose color you want to identify and thus represents the color of interest and represents a color that can be applied to the material of the cosmetic product 10. In some tools, when the user hovers over the pixel, the color code in HTML format (e.g., #F9D4CC) is displayed and when the user is over a pixel that has the desired color, the user then releases the mouse button. The clipboard will now contain the color code in HTML format (or any other format that has been previously specified by the user). This color code can be pasted and used in any text or HTML editor or a color picker tool associated with other software. As shown in FIG. 11, the tool bar 309 can contain an area, such as a box 311, which displays the selected color to make sure the correct selection has been made and that the user is happy with the selection.

Each pixel has a color and each color is represented as a unique number. In many cases, it is a hexadecimal 24-bit number (e.g., #FF0000 represents pure red in HTML). Thus, this tool can be used by the user to easily and quickly obtain color data (a color code) that is used by the device 110 to produce a cosmetic product that has this color. In other words, the device 110 allows the cosmetic products produced with the device 110 to have user chosen customized color(s). The color data is delivered to the device 110 using traditional communication means (including a wired connection or wireless communication means) and a processor or the like of the printer then processes such color data information into print commands that control operation of the device 110.

As mentioned herein, the pixel value is not limited to be a hexadecimal 24-bit number, which is merely representative of one protocol for representing a pixel value, and instead can be based on any other protocol for representing a pixel value.

The color code information can be obtained by other means as well. For example, the user can open a software program and choose a color from an available (displayed) color pallet and then initiate print commands (e.g., as by selecting "print" from a pull down menu) to cause such color code information to be sent to the device 110 for processing and ultimately for applying the necessary inks to create the selected color. Alternatively, as mentioned herein, the user can directly input the color code information into the device if the color code information is already known.

It will be appreciated that the user interface can be part of a mobile device, such as a smartphone or tablet, etc., that is in communication (e.g., wireless) with the device 110. The user can thus view a stored photo on the mobile device and launch an app or run a program that provides the eyedropper tool. As with a personal computer, the user then positions a pointer on an area of the photo that contains the color of interest and the user then obtains the respective color data. This color data can be stored and in combination with other optional input data, such as the specifications (dimensions, product id, etc.) of the resulting cosmetic product, is then communicated to the device 110 to initiate the "printing" (application of the inks, etc.) of the material 14 of the cosmetic component 10.

It will be appreciated that the user interface can be part of a mobile device, such as smartphone or tablet, and launch an app that runs a program that automatically extracts/recommends colors from a select target, such as a photo/image area, such that an eyedropper tool (as described herein) is not needed. More particularly, FIGS. 13-13A illustrate another embodiment in which certain features of the present invention are implemented using an app.

Figure 13:
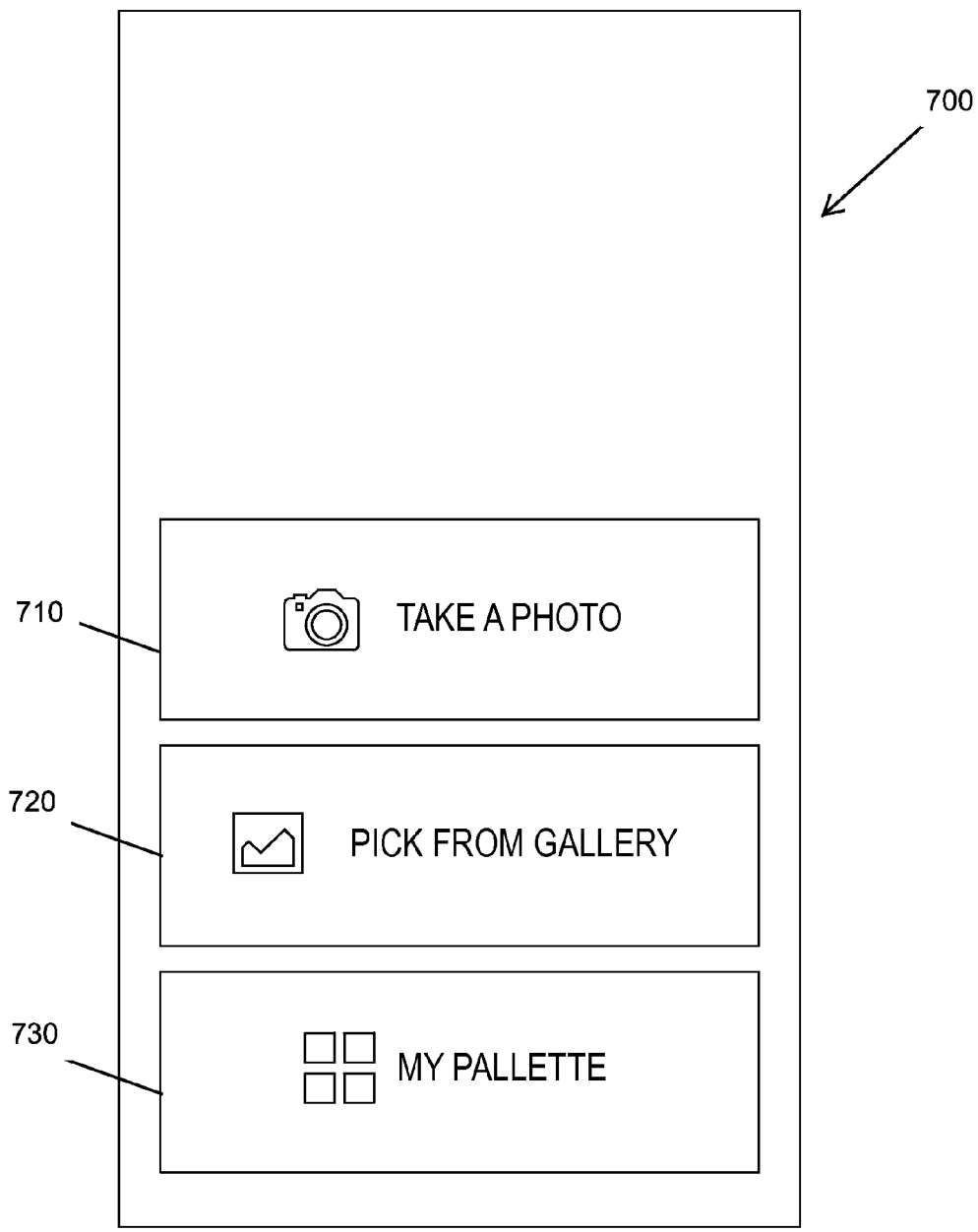
FIG. 13 is a screen shot (home page) of an app for a mobile device.
Figure 13A:
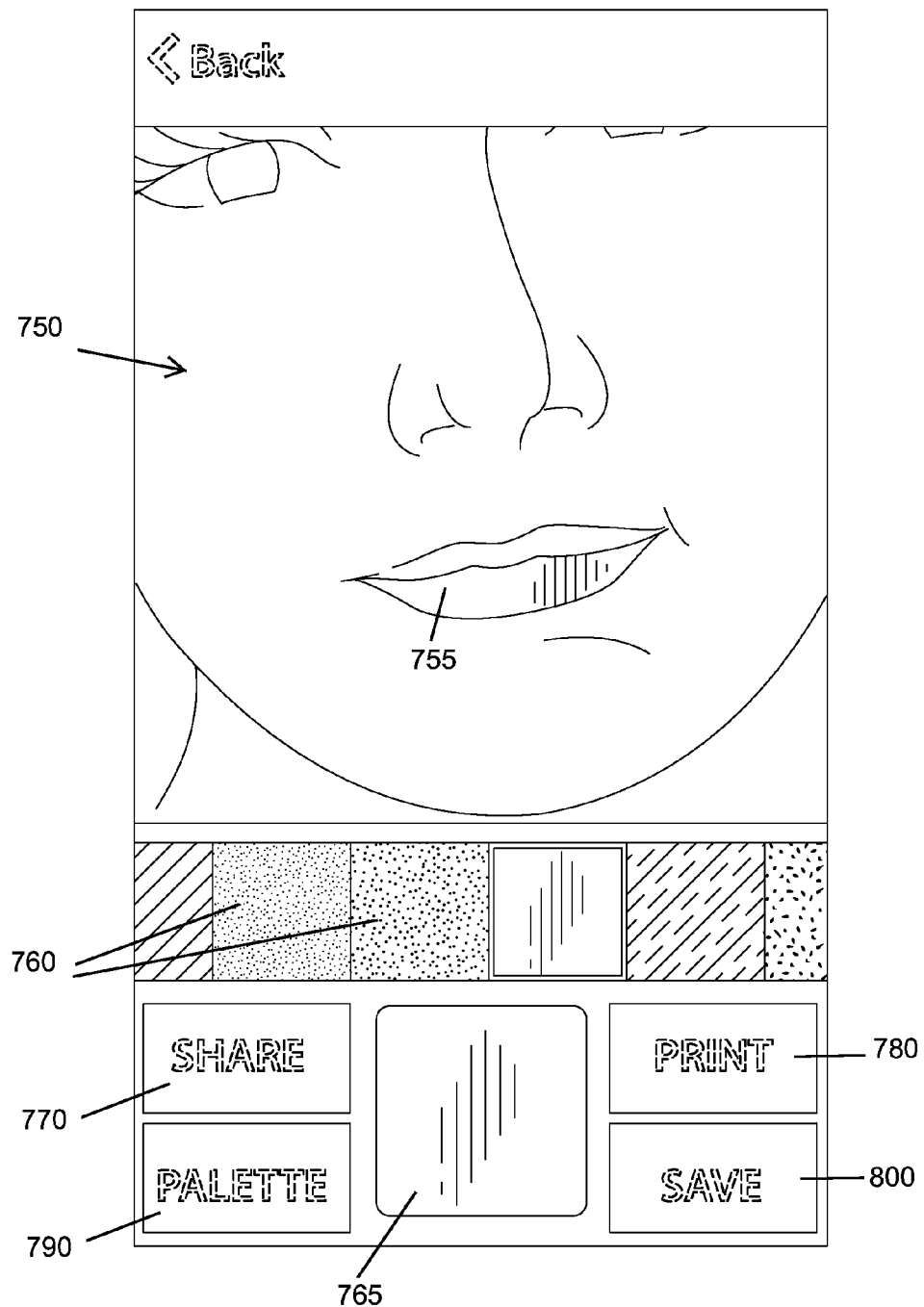
FIG. 13A is an additional screen shot of the app that sets forth color palette listings for selection by the user.

FIG. 13 shows a home screen (home page) 700 of the app. The home screen 700 represents a user interface that allows the user to input information, such as an image. In the illustrated embodiment, the home screen 700 includes a first user input 710 (virtual button), a second user input 720 (virtual button), and a third user input 730 (virtual button). As illustrated, the first input 710 is intended to generate the image by taking a photo. Thus, pressing the first input 710 can instruct the mobile device to launch the camera functionality and allow the user to take a photo of an image of interest using the camera software/functionality. Once the photo is taken, the photo is stored in memory and in this case, the photo is then analyzed using the functionality of the app as discussed below to extract color information relating to the stored image. In particular, the stored photo is analyzed to detect each color that is present in the photo (i.e., the underlying colors that make up the image contained in the photo). In other words, each color that is present in the image is extracted and identified and displayed to the user so that the user can select one of the extracted colors as being the chosen color for creating the custom cosmetic. For example, if the photo consists of a red tulip that includes red petals, a yellow piston and a green stem, then the extracted color information will likely including one or more shades of red, one or more shades of yellow and one or more shades of green since the plant tissue of the stem is likely not one color but comprises multiple shades of green. The display of the color information is described below with respect to FIG. 13a.

The user interface also includes the second input 720 which allows the user to select an image from a gallery of images. Once the user selects an image, the image is analyzed and color information is extracted and displayed as described below and shown in FIG. 13a.

The user interface can also include the third input 730 which allows the user to select a color from a displayed palette. Multiple palettes can be displayed to the user and the user then selects a color from a selected palette. Once the user selects an image from one palette, the image is analyzed and color information is extracted and displayed as described below and shown in FIG. 13a.

FIG. 13a shows one exemplary display of the various color information. In the example of FIG. 13a, the selected image 750 is in the form of a portion of a face and in particular, a pair of lips 755 is part of the image. The lips 755 are adorned with a lipstick that has a color that is of interest to the user. The software then performs a color extraction step in which all colors that are detected in the image (or a selected portion of the image, such as the lipstick) are displayed individually. In FIG. 13a, the various extracted colors (extracted color information) 760 are displayed individually by a series of blocks 760 that are arranged side-by-side. In the event that the number of extracted colors exceed the width of the display, that a navigation tool (such as an arrow(s)) can be provided to allow the user to scroll through all of the extracted colors. The displayed colors can be grouped by colors prior to display on the screen. For example, shades of red can be grouped, shades of browns can be grouped, etc.

To select a color that is presented in the extracted color information, the user simply highlights (presses) the desired block 760 and the chosen color is shown in space 765. As described herein, the color code information is then processed into print commands.

Figure 13B:
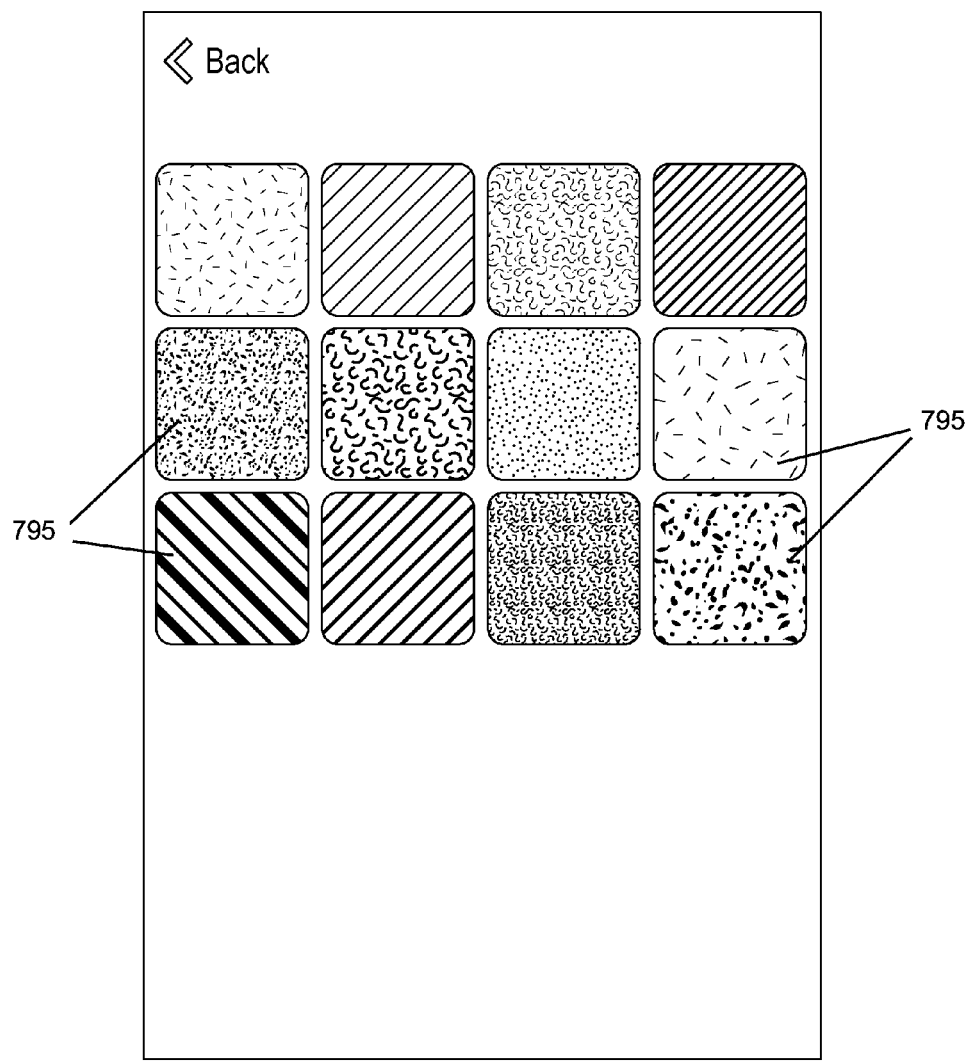
FIG. 13B is an additional screen shot of the app that shows a saved palette.

Other inputs can be part of the user interface, such as a share button 770 that allows the user to share the image (and extracted color information) with others over a network; a print button 780 that allows the user to print the image (and extracted color information) on a connected printer, a palette button 790 which allows the user to save the selected color to memory (storage) as shown in FIG. 13b (saved palette); and a save button 800 that allows the user to save the image in a personalized storage location, such as a personal gallery, etc.

Alternatively, the target (desired) color can be selected from color samples that are stored in a gallery by the user selecting the second input 720. After selecting this menu option, the stored (personalized) color samples are displayed to allow the user to make a selection of the desired color.

Thus, it will be appreciated that the app operates such that after the selected image has been imported, the program (software) automatically extracts all of the color/data code information from the image (e.g., a photo) and this information is presented to the user in an easily readable way so that it is convenient for the user to choose the desired color. As mentioned above, the user can then choose to print, save or share the color. As shown in FIG. 13A, the stored color data can be presented in block form to allow the user to see the various colors from which to choose.

In one embodiment, the app (or other software) is configured to select the various color(s) of the image is that a number of pixels that are selected according to a formula in the image are analyzed. For example, every $n^{th}$ pixel (e.g., $10^{th}$ pixel) in the image is analyzed to collect pixel data (e.g., RGB color data) and each analyzed pixel is then clustered (grouped) into one of a plurality of predefined groups (sets of pixel values) that can be defined by one of the following criteria (values): RGB, CMYK, HSB or other values or color code information. For example, when using RGB criteria is used, the selected pixel has a specific RGB value which is then stored in a specific group. For example, pixels having a predominantly red component are grouped in one pixel set (i.e., the "R pixel set" when RGB is the criteria). Alternatively, the sets can be grouped according to any range on a color spectrum. The limits (e.g., relating to color values) of each group are predefined as by using an algorithm (e.g., the "R" set can include pixel data in which the R value is greater than the other color values (G or B). In addition, the sets can be defined as predfined ranges (subsets) of a color spectrum (the limits of which can be. Only the single color value or the top $n^{th}$ (e.g., 2 or 3) color values that are repeated the most (most predominant) in each set are displayed to the user for selection. This way, colors that are too similar (i.e., the human eye can't really discern the difference) don't get repeated numerous times and only the most prominent color or select number of prominent colors from each set gets displayed. This allows the number of colors displayed to the user for selection to be manageable.

FIG. 13b shows the saved palette that is accessed by pressing the virtual palette button 790. When the saved palette feature is accessed, the colors that have been previously saved by the user (to create the custom palette) are displayed as by a series of blocks (or other shaped virtual button) 795 that arranged side by side. The user can then easily select amongst the colors that were previously saved by the user. In FIGS. 13a and b, different cross-hatching is used to show the different colors.

Once the user makes a selection of the chosen color from any one of the possible ways to do so (i.e., from extracted color information or saved palette, etc.), the software then executes the steps described herein to allow instructions to be sent to the printer (as print commands) for forming the custom cosmetic as described herein. In other words, a color analysis is performed for the selected color and color code information is generated and then used to create print commands.

It will also be appreciated that on a mobile device, simply taking a screenshot/photo of a desired color or zooming into and then cropping into a pixel or set of pixels with the desired color and then printing, the desired color information can be obtained. This is because sometimes the software on the mobile device differs to that of a computer (i.e., it does not resize the image similarly when cropped or zoomed as does a computer).

It will also be appreciated that more than one color can be formed on the material 14 of the cosmetic component 10. For example, the user can use software tools to divide (partition) the surface of the material 14 into more than one section with each section having a different color applied thereto. For example, one half of the material 14 can have one color, while the other half can have a different color. The user can also print custom designs that they can apply directly to the body/face to eliminate the need for skill or time for application.

The software that is executed on the personal computer or mobile device can be configured to not only instruct the device 110 on the color data (color formula) but also the processor can calculate an optimal amount of the cosmetic substance (ink(s)) to be applied to the substrate (material 14) based on the specifications, including the thickness, of the material 14 held in the well of the cosmetic component 10. The location of the substrate (cosmetic component 10) is also know and thus, after these calculations are complete, the cosmetic substance (e.g., ink) is applied onto the top surface of the cosmetic substance 10 at an amount that allows for the cosmetic substance to be uniformly dispersed in the substrate so that the color of the final cosmetic composition that is formed uniform.

In alternative embodiments, the print head can be sized and/or operated so as to deposit material (ink) onto only a select section of the substrate. This select section can be selected by the user using software as described herein. More specifically, once the user inputs identification information concerning the type of substrate or the device 110 includes a means (sensors, etc.) for determining the size and position of the substrate, the user can then select the section to deposit the material (e.g., as by using interactive software and the display screen). For example, the user can highlight on a screen the area for deposit within an image of the boundary (perimeter) of the substrate that is displayed on the screen. The user can use a tool to highlight and define such area for deposit.

After the cosmetic composition is formed, it is then removed from the interior of the device 110. For example, the user can simply insert his or her hand through the opening 120 and retrieve the cosmetic composition 10. The cosmetic composition 10 is now ready for use and has the color chosen by the user.

Not only can the user create a variety of different cosmetic products using the device 110 that have the custom, personalized color chosen by the user, but also, the cosmetic products are produced at much lower cost compared to the retail environment. For example, the user can purchase a number of base substrates 10 that are preferably individually packaged to preserve the individual substrate material or provided in cartridge form. When the user wants to prepare the cosmetic product (cosmetic composition), the user opens up one package and takes out the substrate 10. The substrate 10 is the prepared in the manner described above. The base substrates 10 can be packaged in series (perforated bayonet form) in a common package, such as a box. When the well of the substrate 10 contains a gel or liquid or cream, a releasable protective cover (plastic film) is disposed over such material until the time that the user is ready to insert the substrate into the device 110. The protective cover is then simply peeled off to expose the material and the substrate 10 is then inserted into the device 110 below the print head 160. The user can also purchase powder or liquid material in bulk for even more cost savings. Therefore, the user would measure and prepare the desired amount right before use.

An indicator (audio and/or visual) can be part of device 110 and is configured to notify the user that the application of ink and/or other material is complete and that the formed cosmetic composition (e.g., the dyed material 14 on the substrate 10) can be removed from the device 110. A cover or the like can be placed over the substrate 10 to preserve the cosmetic composition. The removed cosmetic composition is then ready for use and can be applied to a part of the human body, such as human skin. The finished substrates can then be placed in cases so that the user can preserve the cosmetics and travel with them or take them along with them. The intended application site for the cosmetic composition depends upon the type of product that is formed and on the type of base material 14 (e.g., application to eye lashes as in eye liner; cheeks as in foundation, etc.).

As mentioned herein, the cartridges 180 can also contain "glamorizing agents" that enhance the final cosmetic product. In one embodiment, the user interface can have a menu that provides different glamorizing agents from which the user can select. Depending upon which glamorizing agents are selected, the processor will determine the precise "recipe" for making the final cosmetic product using device 110. For example, some glamorizing agents may represent finishing agents that are applied after the coloring agents (dyes) are applied to form the desired color of the final cosmetic composition. Alternatively, some glamorizing agents may represent agents that are discharged onto the material 14 of the substrate 10 at the same time the coloring agents are sprayed onto the material 14. Examples of some glamorizing agents include but are not limited to sparkle material, shimmer material, pearlescent material, sealers, etc.

It will be appreciated that the cosmetic component 10 remains stationary during the application of the coloring agents (inks/dyes) and other materials onto the material 14 of the cosmetic component 10. The material 14 and the applied materials can be thought of as being cosmetic substances that when combined form the final cosmetic composition that is ready for use.

Figure 6:
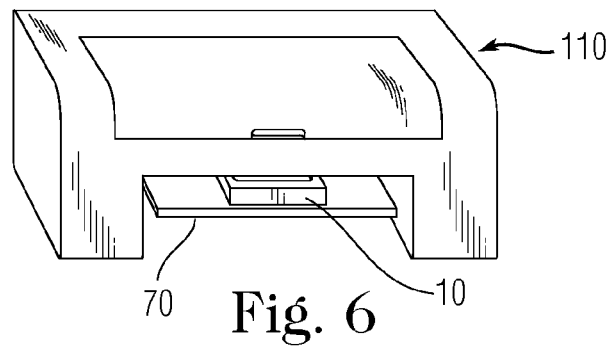
FIG. 6 is a top and side perspective view of a device (applicator) in accordance with another embodiment of the present invention.
Figure 7:
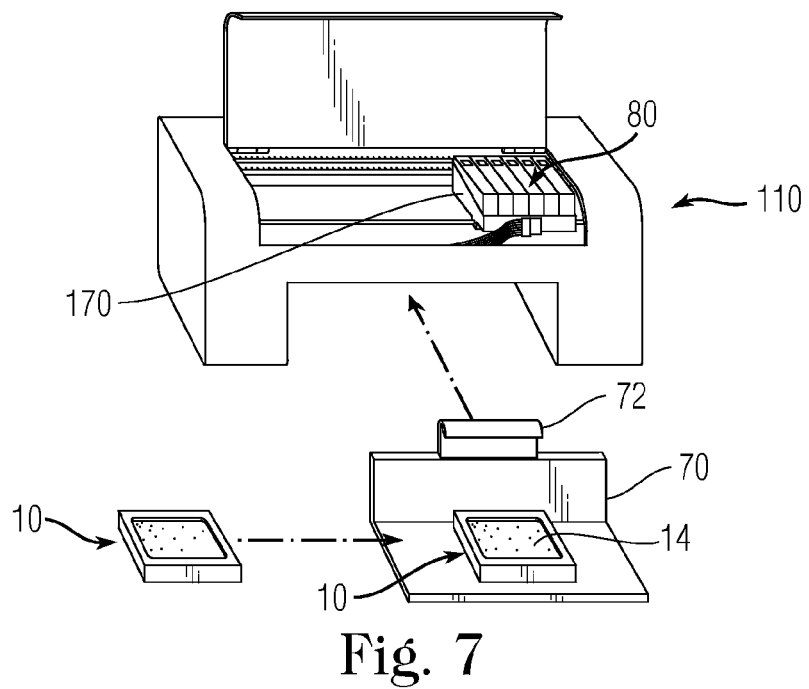
FIG. 7 is a top and side perspective view of the device of FIG. 6 showing a tray for holding the substrate.
Figure 8:
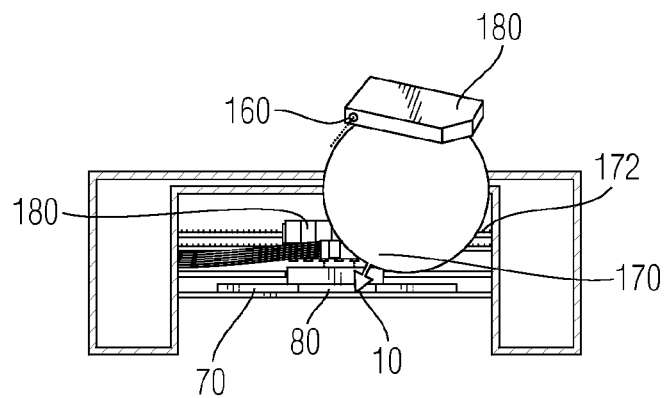
FIG. 8 is a cross-sectional view of the device of FIG. 7.

FIGS. 4-8 illustrate different embodiments of the device 110. In FIGS. 6-8, the substrate 10 is supported by a tray 70 that is inserted into the device 110. The tray 70 can have a locating feature (not shown) for locating and positioning the substrate 10 in the proper location on the tray 70 so that it is disposed underneath the print head 160 when the tray 70 is inserted into the device 110. The tray 70 can have a coupling feature 72 that serves to couple the tray 70 to the device 110 in a manner that ensures that the tray 70 is in a specific, set position relative to the print head 160. This ensures proper registration between the substrate 10 and the print head 160. The coupling feature 72 can be a hook or other structure that mates with a complementary feature in the device 110 to mate the tray 70 to the device 110. The operation of the device 110 in FIGS. 6-8 is essentially the same as the device 110 of FIG. 1.

In yet another embodiment, a heating element (heater) 80 can be provided as part of the device 110 for selectively heating the material 14 of the substrate 10 prior to and/or during the application of the cosmetic substances from the cartridges 180. FIG. 8 shows the heating element 80. For some materials 14, such as waxes, it is desirable to heat the material before applying the cosmetic substances in order to increase the dispersion of the applied substances throughout the material 14.

In addition, it will also be appreciated that the substrate can be in the form of a plastic sheet (e.g., acetate) that receives deposited colors from the ink of the cartridges. After the sheets are left to dry (i.e., water/solvent evaporates), the dye sticks to the sheets and color sheets of the desired color are created which can be easily transported/shipped, and can be converted into the desired cosmetic product with appropriate desired mixing medium (nail, lip, etc.). It will further be appreciated that bulking materials, glamourizing agents and other non-dyeing ingredients of the cosmetics product can be added to the product after printing to create the cosmetic product.

It will also be appreciated that the substrate 10 can be in the form of a material, such as a transfer sheet, that receives a cosmetic image formed of deposited colors from the inks of the cartridges 180 in accordance with user instruction. The colored image can then be transferred to the user's skin or other body parts, lashes, etc., by pressing the image thereagainst. The cosmetic image is thus formed on the user by a transfer print step. The shape and dimensions of the image are selected by the user using the user interface.

It will also be understood and appreciated that the device 110 can be modified so as to be able to apply the cosmetic substances (e.g., inks/dyes) directly onto the human body. For example, the floor of the device 110 can include a locating feature for positioning a human body part, such as one or more fingers. The body part is thus positioned below the print head 160 and the device 110 operates in the same manner described above in that one or more cosmetic substances can be applied from one or more cartridges directly onto the human body (e.g., onto the face, finger nails, etc.). The ink can also pass through an attachment/diffuser, like a brush, airbrush-like diffuser, amplifier or filter etc. and then on to the human body.

It will also be appreciated that a cosmetic composition can be also be created using a non-porous/plastic sheet in a traditional inkjet printer with a y-axis or a stationary/x-axis printer described herein with a non-porous/plastic receiving tray. The plastic sheet/tray receives the deposit of ink from the cartridges. After the plastic sheet/tray is removed, base materials, bulking materials, glamourizing agents, varnishes and other non-dyeing ingredients of the cosmetics product are added after printing is completed to create the desired cosmetic product.

Figure 12:
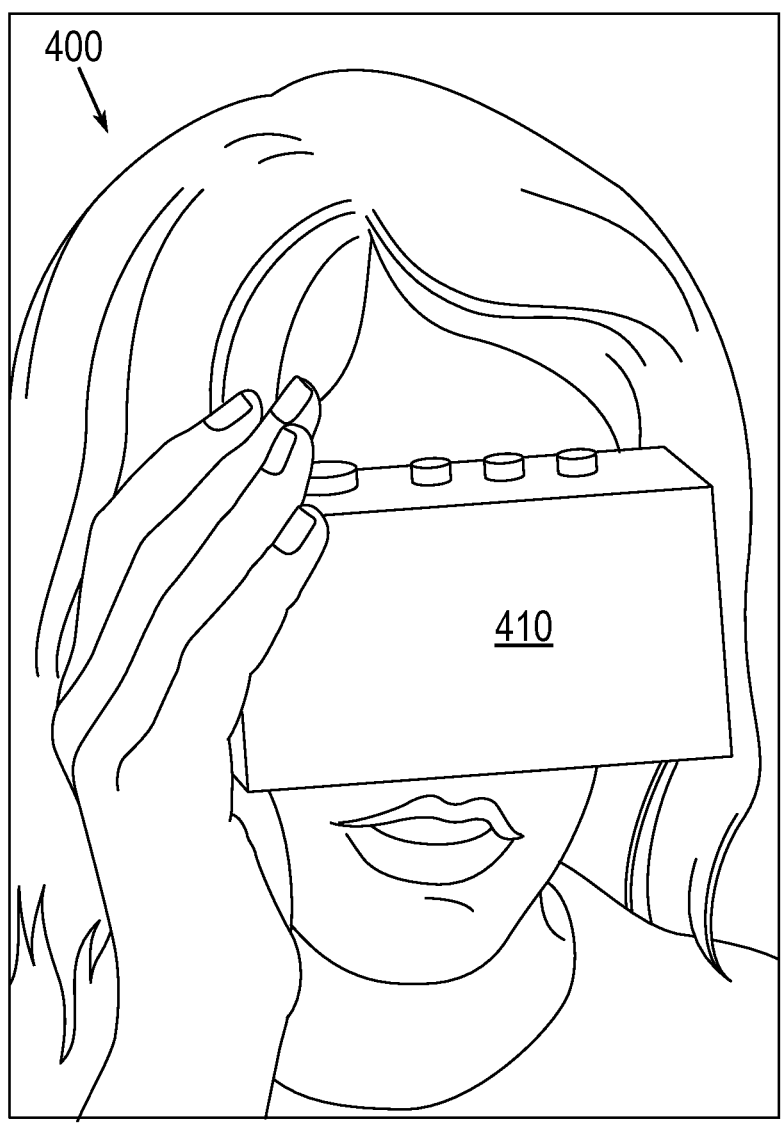
FIG. 12 is an image showing a hand-held device (applicator) in accordance with another embodiment for applying a cosmetic product directly onto the skin.

FIG. 12 shows yet another embodiment of the present invention in which a hand-held device 400 is shown. As discussed herein, the device 400 can share many if not most of the attributes and features described above with reference to devices according to different embodiments, including the table-top printer design. By being hand-held, the device 400 can be easily positioned and disposed against a body part, such as an eye lid, cheek, finger, toe, etc. of the user. Once a command is given by the user, the device 400 applies a predetermined amount of the cosmetic substance onto the target body part of the user.

As shown in the illustrated embodiment shown in FIG. 12, the device 400 has a casing 410 and includes a plurality of controls, such as a power button and one or more actuator buttons, such as a "print" or "apply" button the can be configured to initiate the application process which results in the cosmetic substance being applied to the skin of the user.

The device 400 can also include a display and a user interface which allows the user to control operation of the device 400. The display can be an LCD screen or the like which displays pertinent information and also can include controls (e.g., touchscreen controls, voice controls). The pertinent information can include but is not limited to a display of the selected color.

In this embodiment, the device 400 works similar to the previous embodiments in that after the user selects a color and the color formula is computed, then the printer head operates and dispenses the correct ink (cosmetic substance) or combination of inks to generate a cosmetic substance having the color selected by the user. It will be appreciated that in the hand-held design, the print head does not necessarily have to move to dispense the ink (cosmetic substance) onto the target location of the person but rather, the head can be configured to cause a mixing of the inks prior to being dispense from the device toward the user's body. Alternatively, the print head can operate in the manner described hereinbefore with respect to the previous embodiments in that the print head moves to allow different colored inks to be discharged from the individual cartridges.

The device 400 is intended to be a hand-held device and thus, its foot print accommodates such objective and the device 400 is constructed such that it can be held by a user (e.g., between the two hands of the user).

The device 400 can receive communications from an external source using traditional communications protocol. For example, the device 400 can include a communications port (e.g., a USB port or other type of port) that allows a wired connection to be made between the device 400 and another device, such as a computer. This provides a wired connection between the device 400 and the computer and allows instructions to be sent to the device 400 for preparing one or more custom cosmetic products. The device 400 can also be configured to support wireless communication in that the user can send instructions wirelessly to the device 400 for preparing a customized cosmetic product. For example and as described herein, the user can select a cosmetic type and color using a computer or the like (mobile device) and then utilize software for preparing and then sending instructions to the printer, in this case device 400. The device 400 can thus support wireless communication and the user can use any number of external devices, such as a computer or mobile device (smartphone), to send instructions to the device 400 which are processed and executed by the electronics of the device 400 for preparing and/or applying the cosmetic product. As mentioned herein, the device 400 itself can include a display and user interface (controls) that allow the user to find a color of interest in the manner described herein, such as from a captured photo or a web page each of which can be displayed on the internal display of the device 400. The user then uses the user interface (including tools mentioned herein) to select the desired color and the processor of the device 400 then generates commands that are sent to the printer head in a manner described hereinbefore.

The device 400 can be a two-stage device in that the device 400 can first produce the customized cosmetic product (in the manner described herein) and then the device 400 is operated to physically discharge the just created cosmetic product. The display and/or user controls can signal when the custom cosmetic product is ready to be applied onto the skin of the user. For example, a light or the like can illuminate or a message can be displayed on the display to alert the user that the custom cosmetic product is ready for application. The user can then press a button or the like to cause the application of the cosmetic product.

The device 400 can have any number of other features, such as comfort padding and the like, depending upon the intended application site. For example, as shown in the Figures, if the device 400 is intended to be used against the face, the device 400 is preferably contoured to seat against the face and can include comfort padding that contacts the face when the device 400 is placed against the face.

It will be appreciated that in an alternative embodiment, the device 400 is more of an applicator which is configured to receive a custom substrate 10 that has been previously prepared using one of the devices described previously herein, such as device 100. In this embodiment, the prepared, custom substrate 10 is disposed within the device 400 (e.g., is inserted into a receiving area). The device 400 is configured to dispense the cosmetic substance that is contained within the substrate 10. In this embodiment, the device includes a mechanism (means) for dispensing the cosmetic substance onto the skin. For example, a pusher, brush, or a mechanism (e.g., aerosol based mechanism or airbrush based mechanism) that generates a spray of the cosmetic substance can be used for dispersing the cosmetic substance onto the skin. The type of mechanism may in part depend upon the consistency and state of the cosmetic substance.

The applicator mechanism of the device 400 can be automated or can be manual or can be a combination thereof. For example, once the substrate 10 is inserted into the casing of the device 100, a manual brush mechanism can be used and activated by a button or the like which causes a brush to pick up some of the cosmetic and then be brought into contact with the skin of the user. In an automated version, a motor or the like is used to control the applicator and apply the cosmetic onto the skin.

In this alternative embodiment, the user loads the substrate into the device 400 (e.g., as by opening up a door or tray and loading the substrate) and then once the substrate is in the proper location relative to the applicator, the user initiates the application ("printing") process as by pressing a button or otherwise activating an actuator/controller to initiate the process. An auditory and/or visual alert can be generated to signal to the user that the application process is complete and the user can safely remove the device 400 from the user's body.

While the device 400 can be configured to apply the cosmetic product to the user's face, the device 400 can be designed to apply it to other body parts, such as hands, feet, etc.

The device 400 can also have an alert to indicate that the substrate 10 is running low. For example, a sensor (e.g., optical) can be incorporated to alert the user that the substrate 10 is running low and needs to be replaced. The alert can be auditory and/or visual.

As with the other devices described herein, the device 400 can be configured such that the user may select one particular kind of makeup selected from a plurality of kinds preprogrammed in the device or received from an external source, e.g. from another apparatus, a server, a microcomputer, or a portable telephone. A processor associated with the device can be configured to receive data from another device or from a computer network.

In addition, the device 400 can be configured such that an image or representation of the printing zone is calculated such that the cosmetic substance is applied to this printing zone as opposed to surrounding zones. In particular, the user can undergo an imaging analysis using suitable imaging technology that allows a digital image to be created for one or more target areas of the user. This digital image can then be used by the user to identify and create the boundaries of the target application area (printing zone). For example, a digital camera or the like can be used to take an image of the user's face and then using imaging software and associated tools, the user can identify on the image the printing zone to which the cosmetic Substance is to be applied. For example, if the user wishes to apply a cosmetic product to an upper region of the eye brow bone and crease) or to the eye lid region, the user marks this region on the image of the face/eye. The area highlighted by the user represents the application area/print zone in that the hand-held device 400 is configured to apply the cosmetic substance to this highlighted area. The processor is then configured to determine the surface area of the highlighted region and then dispense an optimal amount of the cosmetic substance to cover the highlighted region as the user uses the device 400 to apply the cosmetic substance to the skin. The processor also knows the borders and boundary of such application area and this ensures proper application.

A display that is part of the device 400 can be used to display the foregoing information.

In yet another embodiment of the present invention, a kit can be provided to the consumer with not only detailed instructions on how to set up and convert a traditional printer into one which can function in the manner disclosed herein and produce custom cosmetic products but also includes the various components needed to produce the cosmetic product, such as the substrate and ink cartridges, etc. The kit can come in any number of different forms including a box or other packaging. With respect to the instructions, the instructions can be in the form of a written instruction and/or a link to a website which includes the instructions on how to convert the printer into one in which custom cosmetic products can be produced. Since there are a significant number of different printers that are commercially available, there will be multiple sets of instructions that correspond to the different types of printers. When a link to a website is provided, the website can provide a listing of different printers from which the user can select.

For each printer, specific instructions are provided for how to convert the printer out of the box into a printer that can be used to produce the customized cosmetic products disclosed herein. For some brand new printers, the conversion is likely quite easy and may involve very few steps. In general, besides switching the ink source to those ink substances described herein that are suitable for forming the cosmetic products, the printer may need to be modified in order to receive any one of the substrates described herein which can receive the cosmetic substances from the ink cartridges via the print head.

The other aspect of the kit is that the kit includes the various parts that are needed to produce the cosmetic products. More specifically, the kit can include the substrate on which the customized cosmetic product is formed and the ink cartridges that contain suitable ink used in the manner described herein. The kit also includes tools and the like like for modifying the out of the box printer into one which can prepare the customized cosmetic products disclosed herein. The contents of the kit can thus be specific to one or more types of printers or the contents can be more universal to allow a selection of the proper tools that one may need for a specific printer.

The aforementioned kits allow a consumer to retrofit a traditional printer for cosmetic applications as described herein.

In particular and according to one embodiment, a conventional printer can be modified for use in the present invention. As discussed herein, the substrate is not advanced using traditional printer mechanisms, such as paper feeding mechanisms, like paper rollers, etc., and therefore, these feeding mechanisms are not used. Traditionally, below the print head and proximate the paper rollers is a platform on which the advanced paper rests as the print head operates. This platform can be modified by placing a hole (well) therein that is sized and configured to receive the substrate. When the substrate is disposed within the hole (well), the top surface of the substrate faces and is positioned proximate the print head just as paper is located during a traditional printing operation.

The location of the hole (well) is thus at a precise location which has and is characterized by a set of specific location coordinates. These location coordinates are used by the computer to instruct the printer (using the protocol described hereinbefore) to print only at the location at which the substrate is located. This is similar to when a spot on a page image of a word processor includes text/an image and this location is fed to the printer software (drivers) to cause the printer to print at said location.

Since paper is not advanced when the printer is retrofitted to print cosmetic substances as described herein, the traditional printer can further be modified by disabling the out of paper sensor. Traditionally, a printer includes some type of out of paper sensor that detects when no paper is in the feed tray. For example, the out of paper sensor can be a contact sensor or optical sensor or another type of sensor that is configured to detect paper in the feed tray. The retrofitting kit can include a means for disabling the paper sensor. Depending upon the type of sensor, the means can be in the form of a spacer that separates contacts (keeps a switch open) or even be part of a special initial paper sheet that is fed through the printer first using the conventional rollers. For example, this special paper sheet can include an adhesive or other block member that is laid down over the paper sensor to effectively disable the paper sensor. Any of these techniques and others can be used to effectively trick the printer into thinking that there is paper, thereby avoiding an error message and ensuring operation of the printer.

In yet another aspect, the software can be configured to control the dispensing of the cosmetic ingredient(s) onto the substrate. As described herein, the printer software knows the precise location of the substrate and the print head is instructed to only print at this location directly onto the substrate. The software can be configured to dispense multiple loads of cosmetic ingredient(s) onto the substrate at specific timed intervals that provides enhanced penetration of the applied cosmetic ingredient. For example, a first application can lay down a first load (first amount) of cosmetic ingredient across the substrate (e.g., the cosmetic ingredient can be applied across the entire top surface of the substrate). A second application of the cosmetic ingredient can be applied after a predetermined first interval of time passes. The second application can be identical to the first application in that the same cosmetic ingredient is applied. The process can be repeated a number of times to successively dispense cosmetic ingredient onto the substrate. As the cosmetic ingredient is applied, the substrate surface is agitated due to the dispensing of the cosmetic ingredient(s) directly onto the substrate. The timed intervals between the dispensing actions allow the applied ingredient to further migrate within the substrate so as to seep downwardly for example. However, this time period is not enough time for the applied ingredient to settle (harden, etc.). The successive applications (successive spraying) of ingredients in effect applies ingredient onto an agitated surface resulting in improved migration of the ingredient throughout the substrate.

The software can be configured such that the user can specify a value which is associated with the number of applications of the cosmetic ingredient(s). The execution of this feature can take many forms since the print drivers are merely instructed to perform multiple print head passes over the substrate at specific, set time intervals. It will also be appreciated that the second and successive applications can cover different surface areas of the substrate compared to the first application of the cosmetic ingredient. For example, if the original print area is a rectangular or square (due to the substrate shape) having a first size, then the first application is typically in the same shape of the same size; however, the successive applications are not limited to being an application over the same surface area. For example, one of the subsequent applications can still cover a square shaped area of the substrate; however, this square shaped area can be of less area than the original square shaped application.

Once again, the successive applications of cosmetic ingredient create a cycle of successive surface agitations with periods of relaxation between the agitation periods. This cycle allows increased control over the application of the cosmetic ingredient.

In one embodiment, the successive printing steps can be presented as a printing of a single piece of paper that has a plurality of print areas of selected color, with the print areas being location in the location coordinates of the substrate and being located in spaced relationship (in different rows) of the paper. In other words, the print images are located in the same column and in spaced rows of the "paper" image that is displayed on the screen and is translated into instructions for controlling the print drivers for printing of the substrate.

This successive printing results in increased saturation of the cosmetic ingredient in the substrate resulting in more uniform application.

Figure 14:
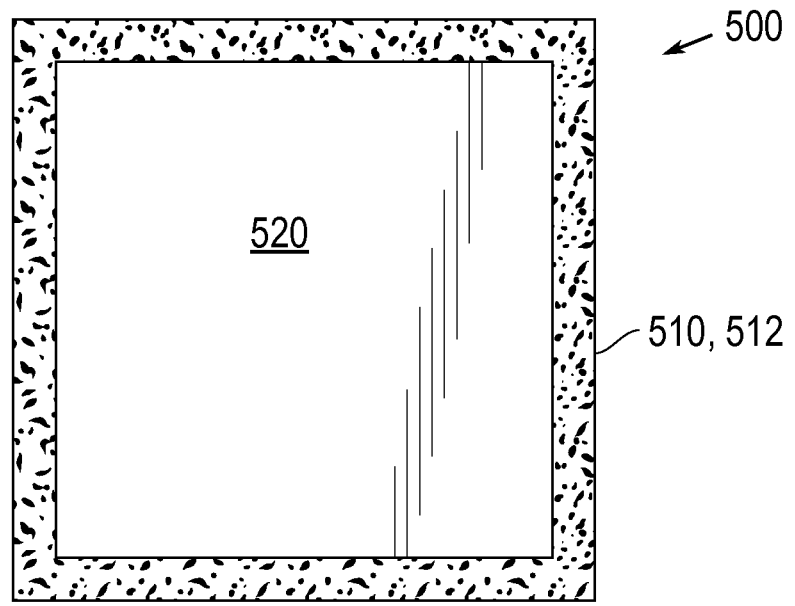
FIG. 14 is a top plan view of a cosmetic product made in accordance with the present invention.

Now referring to FIG. 14 in which another aspect of the present invention is shown. In particular, a cosmetic substrate 500 is illustrated. The cosmetic substrate 500 can be thought of as a makeup sheet for custom generation and use by a user. The cosmetic substrate 500 includes a base layer 510 on which the custom cosmetic product is disposed (applied) as described herein. The base layer 510 can be formed of any number of suitable materials including but not limited to a paper layer, a thin film (e.g., synthetic material), thin foam structure, or the like. As described herein, the base layer 510 and the substrate 500 for that matter are formed such that it can be fed through one of the systems/devices (e.g., printer 110) disclosed herein and therefore, the base layer 510 is flexible and able to be fed through and around rollers and the like as part of the application (printing) process. The base layer 510 includes a protective cover 512, such as a piece of flexible plastic, that covers the top of the base layer 510. The protective cover 512 can thus be a clear plastic film or the like. The protective cover 512 serves at least two purposes in that the cover 512 initially protects the virgin base layer 510 before any application of cosmetic substances and then after the custom cosmetic product 520 is applied to the base layer 510, the cover 512 can be replaced so as to cover the applied cosmetic product 520 so as to allow subsequent reuse of the cosmetic product. To later reuse the product, the user simply lifts the cover 512 from the base 510.

As described herein, the cosmetic material that is applied (e.g., impregnated, coated, etc.) to the base layer 510 can be any number of different types of materials including but not limited to a powder, cream, gel, or any combination thereof. As mentioned above, the base 510 is constructed such that it can be fed through any standard consumer/industrial printer, roller based or flatbed printing or stationary printing (and therefore can be used with any of the devices disclosed herein). It will be understood that the cosmetic product 500 is not limited to being used with the customized printers disclosed herein but can be used with traditional printers so long as the material deposited on the product 500 is suitable for the intended application (i.e., suitable for use as a cosmetic).

In addition, the base layer 510 can include a layer of cosmetic material that is deposited thereon prior to the base layer 510 being fed through the printer. For example, the dried white or clear cosmetic material can be deposited on the base layer 510 and then additional materials, such as dyes, are applied thereto to form the final cosmetic product. The coated base layer 510 must be able to be fed through the printer without being marred and without causing excessive material transfer to the printer equipment also. At the printhead location, other cosmetic ingredients are added (e.g., dyes) to produce the custom cosmetic substance. The coated base layer 510 can thus include an initial solid layer deposited on the base layer.

As mentioned herein, the applied cosmetic substances are not just limited to suitable dyes but also can include base materials (foundation material) as well in that the printer can be configured to apply the base material (foundation) first to the base 510 and then apply the proper dyes over the base material to achieve the intended color and form the intended cosmetic product.

The protective cover/sheet 512 is to be peeled/removed when ready to print and then re-used to save the printed cosmetic. Alternatively/additionally, the sheet 512 can have an additional filter layer (similar to a nylon mesh tea bag material/screen printing fabric) in order to create a barrier between the printer machinery and the deposited cosmetic as well as reduce the amount of dust created from the printer print head moving back and forth. The filter sheet should easily allow ink to pass through and deposited on cosmetic ingredients. Alternatively, the filter layer can be a separate sheet/slim envelope which the makeup sheet can be inserted into of affixed on right before printing.

If no filter layer is used then the makeup can be either pressed/sealed with a fixative/combined with a specialty mixture so that transfer of cosmetic ingredients/powder to printer machinery is minimized or eliminated while the paper is passing through and being printed.

In addition, the makeup sheet (base layer 510) can also have an adhesive back in order to make it like a sticker or way of attaching it to another material. The adhesive layer can thus also be covered with a releasable backing layer.

If the makeup sheet 500 is coated, it can be manufactured by a multitude of methods including flexographic printing, gravure printing, screen printing, spray coating, painting, etc. Paper/film/foam backing 510 should be nonabsorbent or there should be an impervious barrier between the paper/film/foam 510 and cosmetic layer (like wax) in order to prevent the paper from absorbing cosmetic ingredients or moisture from ingredients added after printing.

If the cosmetic ingredient is impregnated into paper 510, then it can be incorporated through mixing into the pulp via the manufacturing process of the paper. If can also be impregnated similar to the way plaster is to gauze like cloth to make plaster strips.

How to Use:

Remove clear film (if any) 512 and load makeup sheet 510 into printer feed tray/area. Put on/in filter (if needed). Choose desired color/images/designs to print via mobile/computer/code methods (mentioned hereinbefore with respect to the different systems of the present invention). Press print or send command to printer to engage. After printer is done printing, if deposited cosmetic on the sheet is mostly powder form, it can be transformed into other forms (ex. nail polish, lipstick, cream) of cosmetic compositions by adding appropriate transforming ingredients (e.g., special colorless lipstick base, lip gloss base, nail base etc.). Transforming bases need to be compatible chemically with ink used and deposited cosmetic composition on sheets otherwise undesired colors/cosmetic composition will result. If user wants to save printed cosmetic for later use, then they can reuse the clear film 512 to reseal cosmetic. The formed cosmetic substance on the sheet can thus provide a base material that can be used with other cosmetic additives to form additional products, such as the ones described above.

It will be appreciated that the cosmetic sheet product 500 is thus configured to be fed through a printer, such as one of the ones described herein, which applies the custom cosmetic product and then the release layer 512 can be reapplied to protect the cosmetic product 500. It will also be appreciated that the printing (application) scheme can be configured such that the one base layer 510 can have more than one application regions in that one base layer 510 can receive more than one applied cosmetic product. For example, the base layer 510 can be divided into two or more regions onto which two different custom cosmetic products are applied. For example, the base 510 can be divided into two side-by-side regions onto which two different cosmetic products can be applied. The different cosmetic products can be separated by a buffer region. As described herein, the software executed by the printer can be configured to identify specific regions on the substrate 510 in which the custom cosmetic product is applied. The user can thus select the size of these individual regions along with identify the physical custom characteristics of the cosmetic, e.g., the color, etc. Alternatively, the substrate 510 can be constructed for a single custom cosmetic product.

Figure 15:
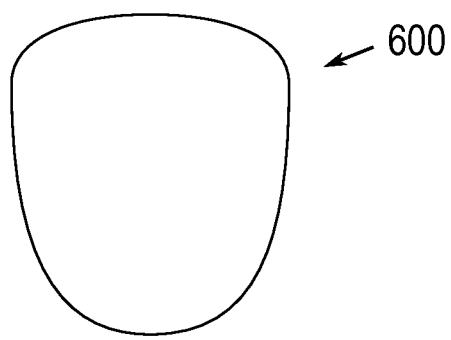
FIG. 15 is a top plan view of a nail sheet in accordance with the present invention.
Figure 16:
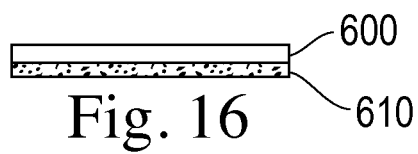
FIG. 16 is a side elevation view thereof.

In yet another aspect of the present invention shown in FIGS. 15 and 16, a blank (white/clear) nail sticker paper sheet (substate) 600 with an ink receptive coating is fed through any standard consumer/industrial printer, roller based or flatbed printing or stationary printing to produce the desired colors/images/designs selected through digital methods on a mobile/computer as described herein. In other words, the nail sticker paper sheet 600 is fed through any of the printer devices described herein. The nail sticker paper can have an adhesive back 610 so that it is easy to affix on the nail. The adhesive material can initially be covered with a removable protective layer (plastic sheet). If there is no adhesive back then nail glue or plain nail polish can be used to stick the paper to the nail. The substrate 600 can be made of a thin film of dried nail polish, vinyl, mylar or any other thin flexible film or paper that can be applied to the nail. The ink receptive coating should be non-toxic and formulated to be allowed to be used in cosmetics as described herein.

Exemplary coatings are commercially available from Ontario Specialty Coatings Corporation. The paper 600 can be a continuous sheet where the user would manually cut out desired shapes after printing or could be pre-cut (such as shapes to more easily fit to nails like traditional nail stickers/wraps. Thus, while element 600 is identified as "paper" it is not limited to being formed of a paper material and instead should be thought of as being a substrate on which the cosmetic substance is deposited.

In this particular application, the substrate paper is customized for application to nails of the user. The applied cosmetic substance is also thus likewise intended for application to the nails of the user.

It will be understood that the above applications are merely exemplary in nature and can be implemented using the modified printer devices disclosed herein. Thus, the software and interactive tools described herein that allow the user to first select a custom color and then formulate the desired cosmetic substance (e.g., cosmetic type (powder, gel, solid, etc.)) and then apply the custom substance to the target substrate.

It will also be appreciated that the cosmetic product that is applied to the base (e.g., base 510 or the nail sheet 600 described above) is not just limited to a colored substance but instead can be in the form of a decorative pattern (indicia) that is applied thereto. In other words, decorative images can be printed (applied) to the substrate (base/nail sheet). For example and with respect to the nail sheet, the decorative image that is to be applied to the nail of the user can take any number of different forms including a flower, butterfly, etc. The printer (which can be a traditional printer or one of the ones described herein) generates the print commands necessary to produce the image on the nail sheet. The printed image is then applied to the nail.

It will be appreciated that the software running the printer can be configured to process these cosmetic substrate sheets in that the sheets have defined areas for receiving ink (cosmetic substances) and can have pre-formed perforations to assist in separation and removal of select sections of the sheet (e.g., one nail sheet).

It will therefore be appreciated that the base material of the custom cosmetic composition can be pre-loaded into the substrate and thus be a part of the substrate or the base material itself can be disposed within a cartridge from which the base material is dispensed (much like the inks/dyes) onto the substrate (which in this case can be a tray or the like). The base material can be applied (e.g., sprayed) either before of simultaneously with the application of the inks and other agents.

It will also be appreciated that the print head can be constructed so as to be stationary within the device (printer) and instead, the nozzles thereof are movable. For example, the print head can be disposed over the target application area which receives the substrate (holder, etc.). Each nozzle associated with the print head can be connected to a mechanism, such as a motor (e.g., servo motor) that allows each nozzle to move in a controlled motion. For example, the nozzle can move in a sweeping motion so as to allow the material being discharged therethrough to spread across target area to ensure proper coverage thereof. Thus, the print head does not move in a side-to-side manner but instead the nozzles move to ensure coverage of the applied material. The motors controlling the nozzles are in communication with a processor that receives set-up input commands in that the size of the substrate is known and is entered so that the sweeping motion or other movement of the nozzles is limited to the target area and does not overreach such area.

For example, if a small sized substrate is being used and the size thereof is entered by the user as by using a user interface, then the motors controlling the nozzles receive commands that results in the motors only being moved a distance that results in the discharged material being delivered within the target area (and not significantly outside thereof).

In addition, the print head can be stationary in a side-by-side manner but can rotate so as to allow each nozzle to be disposed over the substrate to allow for the discharge thereof onto the substrate (e.g., onto the base material in a holder). In other words, the print head can be disc shaped with individual nozzles being formed circumferentially thereabout. Rotation of the print head (as by a stepper motor that allows precise control) and allows for one or more nozzles to be disposed in a target dispensing location relative to the substrate. In the instance where material is discharged from multiple nozzles to form the cosmetic composition, the disc (wheel) will thus rotate in or more steps (increments) to position the requisite nozzles over the substrate and effectuate discharge of the materials therefrom onto the substrate.

In yet another embodiment, the device can include an extrusion, pump or valve mechanism for discharging at least one material onto the substrate (holder). For example, if the base material were contained in a cartridge or the like that is part of the device, the cartridge can be of the type in which the base material is extruded (squirted or applied) through a larger nozzle opening compared to the very small inkjet nozzle openings that the ink (dyes) are delivered. This is because the base material constitutes a large (at least substantially) amount of the final cosmetic composition and thus, the manner in which the base material is applied to the substrate should be efficient. The device can thus have two different ways to discharge material, namely, an extrusion process or similar process, in which the bulk base material is discharged in larger amounts to the substrate and conventional inkjet spray technology (inkjet print head) for applying the dyes and other ingredients. The two mechanisms can be separate within the device or can be integrated into a single print head construction.

Having described preferred embodiments of the systems and the devices (printers) (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims.

What is claimed is:

1. A device for producing a cosmetic composition comprising: a printer having a printer housing that includes at least one print head and an opening for receiving a substrate and positioning the substrate in relation to the at least one print head; and at least one replaceable cartridge that contains a cosmetic substance, the at least one replaceable cartridge being operatively coupled to the at least one print head such that the cosmetic substance can be applied to the substrate through the at least one print head, wherein the substrate contains a base material that can be colored;

a computing device in communication with or is formed as part of the printer, the computing device including a user interface that is configured to allow the user to select a final color of the cosmetic composition, wherein the computing device executes software that is configured to calculate the amount of the cosmetic substance to be applied to the substrate to produce the cosmetic composition based on: the type of the base material that is disposed in the substrate, a total amount of base material in the substrate, and a surface area of the base material in the substrate;

wherein the cosmetic composition is made of at least one cosmetic substance;

wherein the cosmetic composition is a transferable material that can be removed from the substrate and applied to a part of a human body, wherein the cosmetic component comprises one or more coloring agents and the total amount of the one or more coloring agents is an amount of the one or more coloring agents that causes the base material to assume the final color as a result of the one or more coloring agents dispersing uniformly through the base material.

2. The device according to claim 1, wherein
the cosmetic compositions comprises a plurality of cosmetic substances, and
the plurality of cosmetic substances are mixed with the substrate to form the cosmetic composition.

3. The device according to claim 2, wherein the at least one cosmetic substance comprises a coloring agent.

4. The device according to claim 3, wherein each of the cosmetic substances is contained in a separate cartridge.

5. The device according to claim 3, wherein the cosmetic substance further comprises at least one bulking agent and at least one additive.

6. The device according to claim 3, wherein the coloring agent is a material selected from the group consisting of: a natural dye, synthetic colorant, coal tar, chromium oxide, aluminum powder, manganese, iron oxide, mica flakes, a cosmetic color additive and mixtures thereof.

7. The device according to claim 1, wherein the base material is selected from the group consisting of: a solid, a cream, a lotion, a liquid, a gel, an emulsion, a wax, an oil, an ester, and mixtures thereof.

8. The device according to claim 7, wherein the solid comprises one of a packed powder, a loose powder, and a solid material.

9. The device according to claim 7, wherein the ester is selected from the group consisting of: isopropyl lanolate, myristyl lactate and octyl hydroxystearate.

10. The device according to claim 5, wherein the bulking agent is a material selected from the group consisting of: talc, silk powder, silk fiber, nylon, wax, cream, an ester, and an oil.

11. The device according to claim 5, wherein the additive is a material selected from the group consisting of: fragrance, preservative, a pearlescent material, a sparkle material and a shimmer material.

12. The device according to claim 1, wherein each cartridge contains one dedicated print head.

13. The device according to claim 1, wherein the at least one print head contains at least one nozzle through which the cosmetic substance is applied to the substrate, said nozzle being fluidly connected to the replaceable cartridge.

14. The device according to claim 1, wherein the at least one print head is removable to allow one or more nozzles associated with the print head to be cleaned.

15. The device according to claim 1, wherein the computing device executes software that includes a color selection program that allows a user to obtain color data for any pixel of a display screen of the computing device.

16. The device according to claim 1, wherein the color data comprises HTML (hexadecimal) color code information and the computing device includes a printer driver that communicates with printer firmware that allow the HTML color code information to be processed by the printer as printer commands resulting in the printer applying one or more cosmetic substances to the substrate to form the final color.

17. The device according to claim 1, wherein the printer comprises one of an inkjet printer, an extrusion, pump or valve mechanism.

18. The device according to claim 1, wherein the substrate is in a form selected from the group consisting of: a packed powder, a loose powder, a solid, a gel, an emulsion, and a liquid.

19. The device according to claim 1, wherein the substrate remains stationary during application of the one or more cosmetic substances to the substrate.

20. The device according to claim 12, wherein a processor of the computing device calculates an optimal amount of each cosmetic substance to be applied based on a thickness of the substrate and in order to produce the final color.

21. The device according to claim 19, wherein the one or more cosmetic substances are applied to the substrate at an amount that allows for the one or more cosmetic substances to be uniformly dispersed throughout the substrate.

22. The device according to claim 15, wherein the color selection program has a user interface that is configured to allow the user to select a color from an image that is inputted.

23. The device according to claim 22, wherein the color selection program comprises an eyedropper tool that is part of a web browser program to select the color and electronically transfer color code information by identifying an HTML color code of a pixel that is highlighted by the eyedropper tool and then sending print commands to the printer.

24. The device according to claim 22, wherein the user interface is part of a mobile device that executes an app and is configured such that the color is selected by first selecting an image using the app; displaying one or more colors to the user that are present in the selected image; and selecting one of the displayed colors.

25. The device according to claim 24, wherein the color selection program is configured to display one or more colors to the user, the color selection program configured such that target pixels in the selected image are analyzed and for each target pixel, color data values of the target pixel is generated and then based on the color data values, the target pixel is assigned into one of a plurality of groups, and for each group only one or more of the most prominent colors, based on color data values, in the group are displayed to the user for selection thereby.

26. The device according to claim 1, wherein the substrate comprises a plastic holder that has a well that holds the cosmetic composition and a runoff perimeter trench is formed around the well for collecting any runoff.

* * * * *